(12) United States Patent
Laugharn, Jr. et al.

(10) Patent No.: US 9,082,393 B2
(45) Date of Patent: Jul. 14, 2015

(54) ACOUSTIC TREATMENT VESSEL AND METHOD FOR ACOUSTIC TREATMENT

(75) Inventors: James A. Laugharn, Jr., Winchester, MA (US); Carl Beckett, Harvard, MA (US)

(73) Assignee: Covaris, Inc., Woburn, MA (US)

( * ) Notice: Subject to any disclaimer, the term of this patent is extended or adjusted under 35 U.S.C. 154(b) by 616 days.

(21) Appl. No.: 13/422,086

(22) Filed: Mar. 16, 2012

(65) Prior Publication Data

US 2012/0234625 A1 Sep. 20, 2012

Related U.S. Application Data

(60) Provisional application No. 61/453,709, filed on Mar. 17, 2011.

(51) Int. Cl.
*B01F 11/02* (2006.01)
*G10K 11/28* (2006.01)

(52) U.S. Cl.
CPC ............ *G10K 11/28* (2013.01); *B01F 11/0258* (2013.01)

(58) Field of Classification Search
CPC .................................................. B01F 11/0258
USPC .................................................. 366/116, 127
See application file for complete search history.

(56) References Cited

U.S. PATENT DOCUMENTS

| 2,617,874 | A | * | 11/1952 | Lewis ............................ 367/168 |
| 2,632,634 | A | * | 3/1953 | Williams ....................... 366/118 |
| 4,571,087 | A | | 2/1986 | Ranney |
| 6,419,648 | B1 | * | 7/2002 | Vitek et al. ......................... 601/3 |
| 6,432,067 | B1 | | 8/2002 | Martin et al. |
| 7,521,023 | B2 | | 4/2009 | Laugharn, Jr. et al. |
| 2003/0093013 | A1 | * | 5/2003 | Zhong et al. ...................... 601/2 |
| 2007/0053795 | A1 | | 3/2007 | Laugharn, Jr. et al. |

OTHER PUBLICATIONS

International Search Report and Written Opinion for International Application No. PCT/US2012/029404 mailed Aug. 14, 2012.

* cited by examiner

*Primary Examiner* — David Sorkin
(74) *Attorney, Agent, or Firm* — Wolf, Greenfield & Sacks, P.C.

(57) ABSTRACT

Methods and systems for acoustically treating material using a continuous process in which material may be caused to flow in a continuous or intermittent fashion into/out of an acoustic treatment chamber where the material is exposed to focused acoustic energy. The methods and systems may be arranged to permit continuous processing for extended periods while an acoustic energy source operates at a relatively high power output. Treatment chambers may include features such as an acoustic window and/or a chamber wall which may comprise an acoustically reflective material or a gas/wall interface that serves to reflect acoustic energy to form one or more secondary focal zones. Treatment system configurations relating to arrangements of a treatment chamber relative to an acoustic source and coupling medium, material flow paths, and others are provided.

15 Claims, 10 Drawing Sheets

ACOUSTIC TREATMENT VESSEL AND METHOD FOR ACOUSTIC TREATMENT

RELATED APPLICATION

This application claims the benefit of U.S. Provisional Application No. 61/453,709, filed Mar. 17, 2011, which is hereby incorporated by reference in its entirety.

BACKGROUND

1. Field of Invention

The present invention generally relates to the field of treating material with acoustic energy, including systems in which sample material is contained within or flows through a processing zone of a chamber. Aspects also relate to a treatment chamber that is configured to reflect acoustic energy so as to form one or more secondary focal zones within an internal volume of the chamber.

2. Related Art

Ultrasonics have been used for many years for a variety of diagnostic, therapeutic, and research purposes. The acoustic physics of ultrasonics is well understood; however, the biophysical, chemical, and mechanical effects are generally only empirically understood. Some uses of sonic or acoustic energy in materials processing include "sonication," an unrefined process of mechanical disruption involving the direct immersion of an unfocused ultrasound source emitting energy in the kilohertz ("kHz") range into a fluid suspension of the material being treated. Accordingly, the sonic energy often does not reach a target in an effective dose because the energy is scattered in an arbitrary manner (e.g., dissipated prior to reaching the target), absorbed, and/or not properly aligned with the target. Sonication has also hit limits on effectiveness when applied to higher sample volumes or continuous process streams. There are also specific clinical examples of the use of therapeutic ultrasound (e.g., lithotripsy) and of diagnostic ultrasound (e.g., fetal imaging). However, ultrasonics have heretofore not been controlled to provide an automated, broad range, precise materials processing or reaction control mechanism. In U.S. Pat. No. 7,521,023 and others, the use of 'focused acoustical energy' is described to overcome some of the limitations of traditional 'sonication.' Focusing the acoustical energy has many advantages, and can be effective at processing high sample volumes or continuous process streams through the use of a processing chamber through which the sample material passes.

SUMMARY

The inventors have recognized and appreciated that the efficiency of systems and methods for processing samples using focused acoustics can be improved by forming one or more secondary focal zones from acoustic energy within an internal processing volume of the chamber within which a sample is held. For example, acoustic energy may travel through the internal volume of the processing chamber to reach an inner wall surface of the chamber and be reflected back toward the sample so as to form a secondary focal zone within the internal volume of the chamber. The secondary focal zone may be characterized as a region having a greater degree of acoustic intensity than would otherwise be present in the internal volume of the chamber without the occurrence of such reflection from the chamber wall. In prior systems, when unfocused, and uncontrolled ultrasonic energy interacts with a complex biological or chemical system, the acoustic field often becomes distorted, reflected, and defocused. The net effect is that energy distribution becomes non-uniform and/or defocused compared to the input. Non-uniform reaction conditions can limit reaction applications to non-critical processes, such as bulk fluid treatment where temperature gradients within a sample are inconsequential. However, some of the non-uniform aspects are highly deleterious to samples, such as extreme temperature gradients that damage sample integrity. For example, in some instances, high temperatures generated would irreversibly denature target proteins. As another example, when improperly controlled ultrasound is applied to a bulk biological sample solution, such as for the extraction of intracellular constituents from tissue, the treatment causes a complex, heterogeneous, mixture of sub-events that vary during the course of a treatment dose. Accordingly, prior processes are generally random and non-uniform, especially when applied to in vitro applications, such as membrane permeabilization, hindering the use of ultrasound in high throughput applications where treatment standardization from one sample to the next is required. As a consequence, many potential applications of ultrasound, especially biological applications, are limited to specific, highly specialized applications, such as lithotripsy and diagnostic imaging, because of the potentially undesirable and uncontrollable aspects of ultrasound in complex systems.

The use of focused acoustical energy, as described in U.S. Pat. No. 7,521,023 (which is incorporated herein by reference in its entirety) and others, can overcome these limitations, and methods for acoustic treatment of a sample in an enclosed vessel are disclosed. Processing of sample material volumes greater than that of a single vessel can be achieved by transfer of the material into, and out of a focused acoustical 'process zone' or 'treatment chamber'. The material may be resident in the processing zone until the desired result is achieved (single pass), and then transferred to downstream process steps, or captured as a finished product. Alternatively, the material may be recirculated (multi pass) until the desired end state of the bulk material is achieved.

Systems and methods described herein relate to improving the efficiency of focused acoustic processing of samples. In some embodiments, focused acoustical energy is directed toward a sample disposed within an internal volume of a chamber so as to form a focal zone providing focused acoustic treatment. The chamber may be constructed and arranged such that focused acoustic energy having entered into the internal volume of the chamber (e.g., the internal volume defined by an inner wall surface of the chamber) is not significantly transmitted through, dissipated or absorbed into the chamber walls, but rather, is reflected so as to form one or more secondary focal zones within the internal volume of the chamber. Such reflection may expose the sample to further acoustical processing energy. In some cases, reflected acoustic energy that exits out of the chamber travels in a direction such that the acoustic energy does not disrupt function of the transducer (e.g., causing the transducer to shut down). Accordingly, acoustic energy transmitted into the internal volume of the chamber to form an acoustic focal zone is further utilized to process the sample despite having come into contact with the inner wall of the chamber.

In some embodiments, an acoustic energy source emits acoustic energy that results in the formation of a focal zone at a preferred location for treating a sample. The acoustic energy may further travel or emanate from the focal zone within the internal volume of the chamber so as to be reflected off of the surface of the inner wall or otherwise manipulated (e.g., by the geometry defined by the chamber wall). The chamber may be configured such that reflected acoustic energy from the surface of the inner wall remains substantially within the internal volume of the chamber. Acoustic energy that is reflected or otherwise manipulated may form one or more secondary focal zones that further treats sample material in the chamber, for example, by establishing a non-contact, pressure drop environment which aids mixing, disrupting molecular bonds, flowing sample material in a desired direction, etc. Thus, acoustic treatment may be made more efficient, e.g., in part because sonic energy that would otherwise be emitted from the treatment chamber, or else be dissipated, may be utilized for further acoustic treatment in the chamber. Additionally, for some embodiments, reflected acoustic energy does not disrupt function of the transducer via transmission back toward the transducer.

In some aspects, the present invention relates to systems and methods for scaling a process using focused acoustical energy to larger volume batch and continuous process flows, such that the desired result of acoustic treatment can be achieved on larger sample volumes. In fact, flow through processing as described herein can enable some types of acoustic treatment and/or treatment efficiencies that are not possible with non-flow through techniques. The desired result of acoustic treatment, which may be achieved or enhanced by use of ultrasonic wavetrains, can involve without limitation, heating the sample, cooling the sample, fluidizing the sample, micronizing the sample, mixing the sample, stirring the sample, disrupting the sample, permeabilizing a component of the sample, forming a nanoemulsion or nano formulation, forming a liposome, forming a nanosuspension, enhancing a reaction in the sample, solubilizing, sterilizing the sample, lysing, extracting, comminuting, catalyzing, and selectively degrading at least a portion of a sample. Sonic waves may also enhance filtration, fluid flow in conduits, and fluidization of suspensions. Treatment processes may be synthetic, analytic, or simply facilitative of other processes such as stirring.

For example, altering the permeability or accessibility of a sample material in a controlled manner can allow for manipulation of the material while preserving the viability and/or biological activity of the material. In another example, mixing materials or modulating transport of a component into or out of materials, in a reproducible, uniform, and automated manner, can be beneficial. According to one embodiment of the system, sample processing control includes a feedback loop for regulating at least one of sonic energy location, pulse pattern, pulse intensity, duration, and absorbed dose of the ultrasound to achieve the desired result of acoustic treatment. In one embodiment, the ultrasonic energy is in the megahertz (MHz) frequency range, in contrast to classical sonic processing which typically employs ultrasonic energy in the kilohertz (kHz) frequency range.

In some aspects, the present invention addresses the problem of scaling the application of focused ultrasonic energy to treat larger volumes of material, including continuous processes as well as batch scale processing, and provides apparatus and methods for the non-contact treatment of samples with ultrasonic energy using a focused beam of energy. The frequency of the beam can be variable, can be in the range of about 100 kHz to 100 MHz, more preferably 500 kHz to 10 MHz, and can be focused to a processing focal zone of approximately 10 mm to 20 mm (and possibly of larger size with increases in energy), with the sample material passing through this zone to achieve the desired effect. For example, some embodiments of the present invention can treat samples with ultrasonic energy while controlling the temperature of the sample, by use of computer-generated complex wave trains, which may further be controlled by the use of feedback from a sensor. The acoustic output signal, or wave train, can vary in any or all of frequency, intensity, duty cycle, burst pattern, and pulse shape. Moreover, this treatment can be undertaken automatically under computer control, and can also be linked to instrumentation and measurement feedback from the bulk or output stream. In another example, some embodiments of the present invention can treat samples with ultrasonic energy by relative movement of the sample and the focus of the beam, in any or all of two or three dimensions, to ensure complete and thorough mixing within the processing zone.

In some embodiments, these reflected energies are directed inward to create a process 'zone,' where the energies are directed to a process region. The shape of the chamber geometries can be modified to accommodate a range of pressures within this process zone. This may be desirable for certain materials such as biological samples, where a larger more uniform process zone creates an overall more effective processing since the energy density across a larger integrated volume of material is above a certain threshold.

In one embodiment, an acoustic treatment method includes providing a sample to be acoustically treated into an internal volume of a chamber having a wall with an inner side. The sample may include any suitable material, such as a liquid, solid, mixtures, suspensions or other combinations of liquids and solids, etc. The chamber may have any suitable size, shape or other arrangement, e.g., may be a single isolated vessel or an arrangement that permits flow of material through a space. Acoustic energy, having a frequency of about 100 kHz to 100 MHz, may be transmitted from an acoustic energy source that spaced from the chamber. For example, an acoustic transducer that includes one or more piezoelectric elements may be used to emit acoustic waves having a suitable arrangement to form a focal zone at least partially within the chamber. The acoustic energy may be transmitted through a coupling medium, such as a liquid and/or solid, to the internal volume.

Acoustic energy that might otherwise exit the chamber may be reflected to form a secondary focal zone in the chamber. For example, the chamber may include a wall that is thin, substantially transparent to acoustic radiation and surrounded by air or other gas so as to provide a gas/chamber wall interface. In this embodiment, the gas/chamber wall interface may provide a suitable difference in acoustic impedance or other acoustic property relative to the sample material so that acoustic energy is reflected at the gas/chamber wall interface and back into the internal volume of the chamber. While, in some cases, the inner wall of the chamber may comprise a material that is acoustically non-reflective (e.g., absorbs acoustic energy, acoustically transparent, dissipates acoustic energy), when the acoustically non-reflective material is sufficiently thin and the outer wall forms an interface with a composition having a substantially different acoustic impedance as the acoustically non-reflective material, the interface may be acoustically reflective. That is, a contrast in acoustic impedance between two different materials (e.g., plastic and air) provides an arrangement that suitably reflects acoustic energy. For instance, the chamber wall may include a thin wall of plastic or glass (e.g., having a thickness less than 1 mm) where a gas (e.g., air) is disposed on a side opposite the internal volume of the chamber, giving rise to reflection of acoustic energy. On the other hand, when acoustic energy impinges against a thicker wall of acoustically non-reflective material (e.g., having a thickness greater than 1 mm), such as plastic or glass, the material would tend to transmit, absorb or dissipate acoustic energy from within the internal volume of the chamber, resulting in a comparatively smaller degree of overall acoustic energy utilization. By reflecting acoustic energy from the inner wall of the chamber in a manner that substantially retains, or recycles, the acoustic energy within the internal volume of the chamber, acoustic sample processing may be made more efficient.

In an alternative embodiment, the chamber wall material itself could be made from a high impedance material that is intrinsically acoustically reflective (e.g., stainless steel, other reflective metals, conductive materials, etc.), thus causing direct reflection back into the processing zone; in contrast with acoustically non-reflective materials that transmit, dissipate or absorb the acoustic energy. In this respect, no matter how thick the wall of acoustically reflective material, the acoustic energy will be reflected, although the thickness or geometry of the acoustically reflective material may affect how the acoustic energy is reflected off the inner wall (e.g., contributing to the size and location of one or more secondary focal zones) and in which direction the reflected acoustic energy travels.

In another illustrative embodiment, a system for treating a material with acoustic energy includes a chamber having a wall with an inner side defining an internal volume and arranged to cause reflection of acoustic energy in the chamber to form a secondary focal zone in the chamber. An acoustic energy source may be spaced from the chamber and arranged to emit acoustic energy having a frequency of about 100 kHz to 100 MHz to create a focal zone of acoustic energy in the internal volume. A coupling medium, e.g., including a liquid and/or a solid, may be arranged to transmit acoustic energy from the acoustic energy source to the internal volume. The chamber may optionally have an opening into the internal volume (e.g., at a bottom of the chamber), an inlet to receive an inflow of material into the internal volume and an outlet to discharge an outflow of material from the internal volume. In some embodiments, the internal volume of the chamber is fully enclosed, without an inlet or outlet (e.g., in a single use consumable vessel). For example, the chamber may have a window that permits transmission of acoustic energy having a frequency of about 100 kHz to 100 MHz through the window, yet is completely closed to fluid flow into or out of the internal volume.

In one embodiment, the chamber wall may be substantially transparent to acoustic energy having a frequency of about 100 kHz to 100 MHz. A window may be provided in the opening of the chamber and be arranged to sealingly close the opening and to transmit focused acoustic energy into the chamber for treatment of material in the internal volume. The window, which may be formed unitarily, integrally or otherwise with the chamber wall, may be generally transparent to acoustic energy having a frequency of about 100 kHz to 100 MHz. A housing may be attached to the chamber and window so that the window is exposed at a lower end of the housing, and the chamber is located in an inner space of the housing. This arrangement may allow the housing to maintain contact of an outer side of the chamber wall with a gas in regions above the window, e.g., where the lower end of the housing and the window are submerged in a liquid coupling medium. An interface between the chamber wall and the gas, or the chamber wall itself, may have a focusing affect on acoustic energy in the internal volume to create one or more secondary focal zones of acoustic energy in the internal volume. For example, acoustic energy that is scattered or otherwise emitted from the focal zone created by the acoustic energy source may be reflected by the chamber wall (e.g., having an acoustically reflective material or interface) back into the internal volume for the creation of the secondary focal zone(s).

In some embodiments, an inner wall of the chamber has an acoustically reflective material or interface (e.g., glass/plastic and air interface) formed into or with structural elements that may cause reflected acoustic energy to form one or more secondary focal zones within the internal volume of the chamber. Structural elements may include, for example, any combination of grooves, ridges, steps, jagged/curved edges, protrusions, depressions, etc, that may function to direct acoustic energy within the internal volume. For example, such structures may serve to guide the acoustic energy in a particular direction (e.g., away from the exit of the chamber, away from the transducer, toward a certain region of the internal processing volume, etc.) or to form multiple secondary focal zones having various shapes and sizes (e.g., spherical, ellipsoidal, line, cigar-shaped, planar, etc.). In some embodiments, structural elements disposed along the inner wall of the chamber may have a curvature that directs reflected acoustic energy toward a central or uppermost region of the internal volume of the chamber, or to another suitable location within the internal volume. In some embodiments, the chamber may have a dome shape, e.g., that includes a hemispherical portion, cylindrical portion, conical portion or other suitable shape to help focus or otherwise direct sonic energy. In one embodiment, an optional outlet to discharge an outflow of material from the internal volume may be located at an uppermost portion of the chamber, e.g., to help remove gas from the internal volume that is liberated during the acoustic treatment. This may help prevent interference of gas in the chamber with the acoustic energy. Additionally, it may ensure larger/heavier particles remain in the process zone until they are small enough to become buoyant and travel with the outgoing sample. In one embodiment, an optional inlet to the chamber may intersect from the top of the chamber, but have an inlet tube that extends in the inside of the chamber to the bottom region, thus ensuring material must pass through the processing zone on its way to the outlet. This arrangement may be more important in a low flow and/or a low acoustic energy processing conditions.

In another aspect of the invention, a system for treating a material with acoustic energy may include a chamber having a wall with an inner side defining an internal volume and an outer side opposite the inner side that is substantially surrounded by a gas. An interface of the gas with the outer side of the chamber wall may help to reflect or otherwise direct acoustic energy in a manner that limits the acoustic energy from exiting the chamber and/or to create one or more secondary focal zones. One or more secondary focal zones formed of reflected acoustic energy may complement the focal zone created by the acoustic energy source, e.g., to aid in the acoustic treatment of the sample material. In one illustrative embodiment, the chamber may have a dome shape, e.g., with the upper portion of the dome arranged at a top of the chamber and farthest from the acoustic energy source. The dome shape of the chamber may be arranged to focus or otherwise direct acoustic energy to form a secondary focal zone. The chamber may have an opening into the internal volume, an optional inlet to receive an inflow of material into the internal volume and an optional outlet to discharge an outflow of material from the internal volume. In one embodiment, the chamber wall may be substantially transparent to acoustic energy having a frequency of about 100 kHz to 100 MHz, have a thickness of about 0.010 inches, and may be made of a polyethylene, PET, Teflon/FEP based, TPX (polymethylpentene), or other suitably acoustically transparent material. A window may be located at the opening of the chamber and be arranged to seal close the opening and to transmit focused acoustic energy into the chamber for treatment of material in the internal volume. The window may be generally transparent to acoustic energy having a frequency of about 100 kHz to 100 MHz, e.g., to help prevent loss of acoustic energy, heating of the window, etc. For example, the window may be formed of polyimide (e.g., KAPTON). An acoustic energy source may be spaced from the window and the chamber and arranged to emit acoustic energy having a frequency of about 100 kHz to 100 MHz to create a focal zone of acoustic energy in the internal volume. A coupling medium, e.g., including a liquid and/or a solid (which includes deformable materials such as gel, silicone and others), may be arranged to transmit acoustic energy from the acoustic energy source to the window. In one embodiment, the window may be in contact with the coupling medium, e.g., the window and other lower portions of the chamber may be submerged in a water bath or viscous gel (e.g., hydrogel). A housing may be attached to the chamber and window so that the window is exposed at a lower end of the housing and the chamber is located in an inner space of the housing. This arrangement may allow part of the housing to be submerged in a liquid coupling medium, placing the window in contact with the coupling medium. However, the housing may maintain a gas in contact with chamber wall even though parts of the chamber wall may be located below a top level of the coupling medium. The chamber and window may be arranged to maintain a pressurized environment in the internal volume, e.g., to help reduce cavitation, or to pull a vacuum to reduce gas content in the internal volume.

In some embodiments, the chamber can be sealed and have one or more inlets and outlets to the chamber for effective transfer of the bulk fluid material through the chamber. The chamber can be sealed during the treatment to prevent contamination of the sample material or of the environment. In some embodiments, arrays of chambers can be used for processing multiple sample streams in parallel, where very large sample volumes are needed, such as in manufacturing process streams. In some embodiments, the chambers and/or other components that contact a material processed may be made in a disposable form, e.g., for one time use in processing a material and discarded thereafter. The inlet and outlet may be located near a top of the chamber, and thus, the internal volume of the chamber may, in some sense, depend from the inlet and outlet or otherwise be positioned below at least the outlet. The inlet and outlet may each include a conduit that extends away from the chamber so that material may be introduced into the chamber even though the chamber may be otherwise completely sealed from an external environment. Flow of the material may be caused by a pump, gravity or other motive force, and the first and/or second conduits may be connected to a respective reservoir that serves to hold material as necessary.

The system may be arranged to accommodate continuous acoustic treatment of material in the chamber for an extended time period, e.g., for 1 hour or more, at a relatively high intensity, e.g., at an output of the acoustic transducer of 200 watts or more, without experiencing excessive heat buildup or other problems. For instance, in a continuous acoustic treatment, material may be caused to flow in a continuous fashion in a chamber, or may flow in an intermittent fashion. Also, the acoustic energy source may operate at a power level that varies, but on a time averaged basis operates at a relatively high power output level, e.g., 200 watts or more. This is in contrast to prior acoustic treatment arrangements in which continuous acoustic treatment for 1 hour or more could not have been achieved for a variety of different reasons, such as excessive heat buildup, failure of the acoustic source, damage to the sample material, and so on.

In some arrangements, the internal volume may be suitably sized or otherwise arranged to help expose material in the internal volume to the acoustic energy. For example, the internal volume may include walls that are located near the boundaries of an acoustic focal zone in the internal chamber to help ensure that material is maintained in or near the focal zone during treatment. In other arrangements, the internal volume may include elements that provide nucleation points for cavitation or other acoustically-caused affects.

These and other aspects of the invention will be understood from the following description and claims.

BRIEF DESCRIPTION OF THE DRAWINGS

Illustrative embodiments of the invention are more particularly described in the following detailed description, taken in conjunction with the accompanying drawings. In the drawings, like reference characters generally refer to the same parts throughout the different views. Also, the drawings are not necessarily to scale, emphasis instead generally being placed upon illustrating principles of the invention.

DETAILED DESCRIPTION

"Sonic energy" as used herein is intended to encompass such terms as acoustic energy, acoustic waves, acoustic pulses, ultrasonic energy, ultrasonic waves, ultrasound, shock waves, sound energy, sound waves, sonic pulses, pulses, waves, or any other grammatical form of these terms, as well as any other type of energy that has similar characteristics to sonic energy. "Focal zone" or "focal point" as used herein means an area where sonic energy converges and/or impinges on a target, although that area of convergence is not necessarily a single focused point, but may include a volume of varying size and shape. As used herein, the terms "process chamber" or "processing zone" as used herein means a vessel or region where the sonic energy converges, and the sample material is present for treatment. As used herein, "nonlinear acoustics" can mean lack of proportionality between input and output. For example, as the amplitude applied to the acoustic transducer increases, the sinusoidal output loses proportionality such that eventually the peak positive pressure increases at a higher rate than the peak negative pressure. Also, water becomes nonlinear at high acoustic energy intensities, and in a converging acoustic field, the waves become more disturbed as the intensity increases toward the focal point. Nonlinear acoustic properties of tissue can be useful in diagnostic and therapeutic applications. As used herein, "acoustic streaming" can mean generation of fluid flow by acoustic waves. The effect can be non-linear. Bulk fluid flow of a liquid in the direction of the sound field can be created as a result of momentum absorbed from the acoustic field. As used herein, "acoustic micro-streaming" can mean time-independent circulation that occurs only in a small region of the fluid around a source or obstacle, for example, an acoustically driven bubble in a sound field. As used herein, "acoustic absorption" can refer to a characteristic of a material relating to the material's ability to convert acoustic energy into thermal energy. As used herein, "acoustic impedance" can mean a ratio of sound pressure on a surface to sound flux through the surface, the ratio having a reactance and a resistance component. As used herein, "acoustic window" can mean a system or device for allowing sonic energy to pass through to the sample within the processing chamber or zone. As used herein, "acoustic lens" can mean a system or device for spreading, converging or otherwise directing sounds waves. As used herein, "acoustic scattering" can mean irregular and multi-directional reflection and diffraction of sound waves produced by multiple reflecting surfaces, the dimensions of which are small compared to the wavelength, or by certain discontinuities in the medium through which the wave is propagated.

Apparatus and Methods for Ultrasonic Treatment

Figure 1:
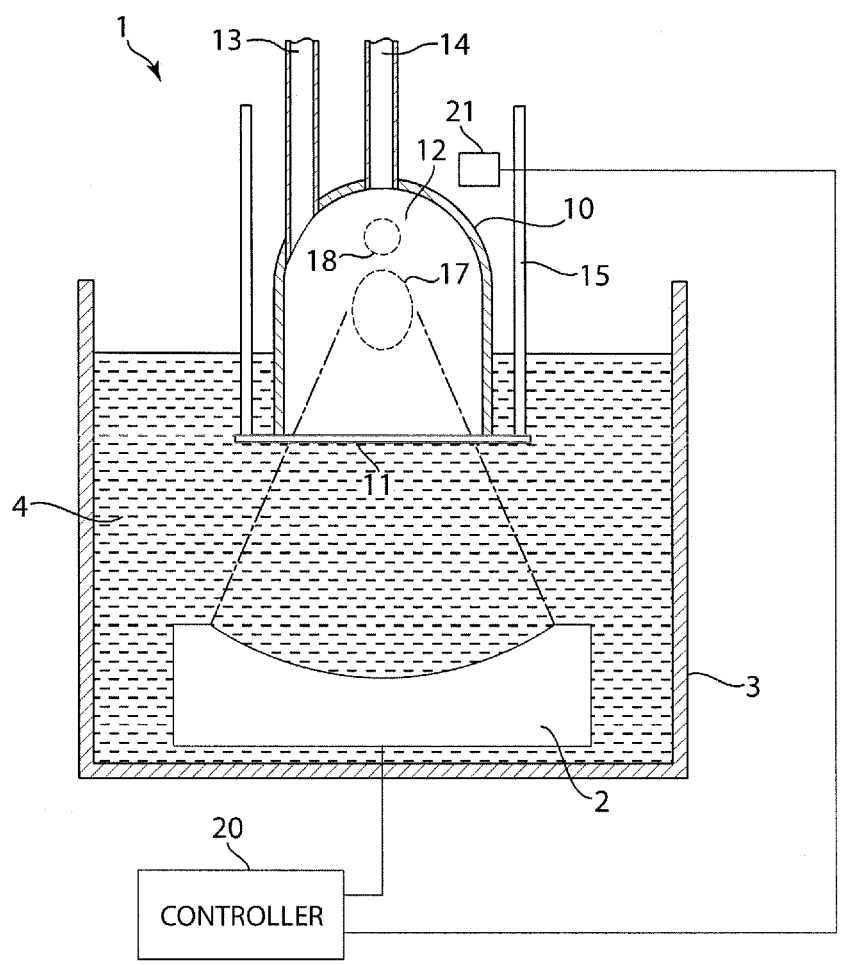
FIG. 1 shows a schematic diagram of an acoustic treatment system in an embodiment.

FIG. 1 shows one embodiment of an acoustic treatment system 1 in which focused acoustic energy generated by an acoustic energy source 2 passes through a coupling medium 4 (which may include a solid and/or a liquid, such as water) to an acoustic window 11 of a chamber 10 and into an internal volume 12 of the chamber 10 where the sample material is located. The acoustic treatment system 1 may include a controller 20 (e.g., including a suitably programmed general purpose computer or other data processing device) that receives control information (e.g., from one or more sensors, user input devices, etc.) and correspondingly controls operation of the acoustic energy source 2 and/or other system components. Sample material is optionally provided into the internal volume 12 via an inlet 13, is acoustically treated in the internal volume 12, and is removed from the volume 12 via an outlet 14.

The acoustic energy source 2 may include an ultrasound transducer that projects a focused ultrasound beam or wave front toward the window 11 of the chamber 10. The window 11, which may sealingly close an opening in the chamber 10, may be suitably transparent to, or otherwise transmit acoustic energy so that the ultrasound beam penetrates the window 11 to form a focal zone 17 within the internal volume 12 that acts upon the sample material in the chamber 10. The window 11 may be configured to transmit a maximum amount of ultrasound energy to the material in the chamber 10, and/or control heat transfer between the internal volume 12 and, for example, an external water bath or other coupling medium 4. In certain embodiments, the window 11 is glass, sapphire, quartz or a polymer such as a polyimide (e.g., KAPTON) or polymethylpentene. The window may have any suitable shape or other configuration, e.g., may be flat (or otherwise present a relatively flat surface to the impinging acoustic energy), or may be curved so as have a hemispherical or other convex shape, thereby allowing the acoustical energy to pass at an approximately 90 degree angle from the converging acoustic field. In certain embodiments, the window 11 is shaped to guide the sonic energy in a preferred manner relative to the internal volume 12, such as focusing or defocusing the acoustic energy, through a 'lens' effect caused by the physical shape of the window 11 (such as an effect caused by a concave or convex shape or other lens configuration). In some embodiments, the window 11 has an acoustic impedance similar to that of water (or other coupling medium 4) and a relatively low acoustic absorption. One preferred material is low density polymethylpentene, but other polymers such as polypropylene, polystyrene, poly(ethylene terephthalate) ("PET"), polyimide (e.g., KAPTON), and other rigid and flexible polymers may be used. If the window 11 is formed from a thin film material, the film may be a laminate to facilitate thermal bonding to the chamber 10, and/or may have a thickness of about 0.1 to 0.5 mm (e.g., 0.25 mm). For example, the window 11 may be sealingly attached to the chamber 10 using heat sealing, adhesives, mechanical clamps, or other fasteners, or other arrangements, or may be sealed using common gaskets or O-ring concepts. Thicker, more rigid materials may also be employed for the window 11.

The chamber 10 may include a wall with an inner surface that defines the internal volume 12. In one aspect of the invention, the wall may have an outer surface that is substantially surrounded by a gas (such as air) or another material that has an acoustic impedance that is significantly different from an acoustic impedance of the chamber wall and/or the sample material. In some embodiments, the chamber wall may be made relatively thin, e.g., having a thickness of about 0.001-0.1 inches (e.g., 0.010 inches), and may be substantially acoustically transparent. Thus, an interface between the gas (or other material having an acoustic impedance that differs from the acoustic impedance of the chamber wall) around the outer surface of the chamber wall and the chamber wall itself may function to reflect acoustic energy back into the internal volume 12. The chamber wall may include any suitable acoustically non-reflective material, such as but not limited to glass, sapphire, quartz, plastic, an appropriate polymeric material, or combinations thereof.

In some cases, the chamber wall is relatively thick and is composed of a material that is acoustically reflective, such as an appropriate metal (e.g., stainless steel, conductive material). Accordingly, a thick chamber wall comprising an acoustically reflective material may serve to reflect acoustic energy without requiring the presence of an interface between materials having substantially different acoustic impedance. Thus, in an embodiment, to suitably reflect acoustic energy back toward the sample material, the chamber wall may include a relatively thick stainless steel material without an air gap or other material having an acoustic impedance different from that of the chamber wall disposed immediately adjacent an outer side of the chamber wall. The chamber wall may include any suitable material, such as but not limited to glass, sapphire, quartz, metal, plastic, an appropriate polymeric material, or combinations thereof. Or, the chamber wall may include any suitable acoustically reflective material, such as but not limited to metal, stainless steel, an appropriate reflective material, or combinations thereof.

In various embodiments, acoustic energy in the internal volume 12 may be reflected by the chamber wall, or the chamber wall/gas interface, so as to create a secondary focal zone 18 of acoustic energy. A secondary focal zone, generally, may comprise a region of higher acoustic intensity than would otherwise be present in the internal volume of the chamber absent the reflective chamber wall or interface at the chamber wall. A secondary focal zone may have characteristics that are similar to, or may vary significantly, from a primary focal zone. This secondary focal zone 18 may be coincident with the focal zone 17, or may be located apart from the focal zone 17. Moreover, secondary focal zone 18 may be smaller than, larger or the same size as the focal zone 17, and the chamber wall may be arranged to create two or more secondary focal zones 18. Alternatively, the secondary focal zone may be shaped to act on a larger volume of material, thus creating a higher integrated pressure across that region of material. If focused, the secondary focal zone 18 may have an acoustic energy intensity that is higher (or lower) in relation to the acoustic energy intensity at the focal zone 17. For example, if a peak positive pressure at the focal zone 17 is about 1 MPa (mega Pascal) to about 10 MPa pressure, or about 150 PSI (pounds per square inch) to about 1,500 PSI, the peak positive pressure at the secondary focal zone 18 may be 20% greater than this. (A focal zone is an area in which the acoustic energy intensity is within about 6 dB of the peak acoustic intensity.) In this illustrative embodiment, the chamber wall includes a dome-like shape that is located near a top of the chamber 10, e.g., a portion farthest away from the acoustic energy source 2. This arrangement has been found to suitably reflect and focus acoustic energy to form a single secondary focal zone 18 that is located above the focal zone 17, and can help ensure that sample material is suitably exposed to acoustic energy, e.g., by inducing mixing in the chamber 10 or through other affects. While not expressly shown in the figures, it can be appreciated that the chamber wall may be configured to reflect acoustic energy in a manner that creates multiple secondary focal zones having various shapes and sizes at suitable locations within the internal volume of the chamber.

To help acoustically couple the chamber 10 with the acoustic energy source 2, the window 11 may be placed into contact with the coupling medium 4, whether the coupling medium 4 is liquid or solid. Where the coupling medium 4 is liquid, accommodations may be made to help maintain a gas/chamber wall interface by preventing the coupling medium 4 from contacting portions of the chamber 10 above the window 11. In this illustrative embodiment, the chamber 10 is received in a housing 15, such as a cylindrical sleeve, so that the window 11 is exposed at a lower end of the housing 15, but other portions of the chamber 10 are located in the inner space of the housing 15. For example, the window 11 may be bonded or otherwise attached to the housing 15 so as to form a liquid-tight joint that prevents liquid coupling medium 4 from flowing into the space between the chamber wall and the housing 15. This helps to maintain air or other gas around the chamber wall even if the window 11 and/or portions of the housing 15 are submerged below the top level of the coupling medium 4. That is, at least some parts of the chamber wall, such as the entire chamber 10, may be located below the top surface of the liquid coupling medium 4 while the gas/chamber wall interface is maintained. In FIG. 1, only a lower part of the chamber 10 is positioned below the top surface of the coupling medium 4, but it should be understood that the top level of the coupling medium 4 may be positioned in any suitable way relative to the chamber 10.

Figure 2:
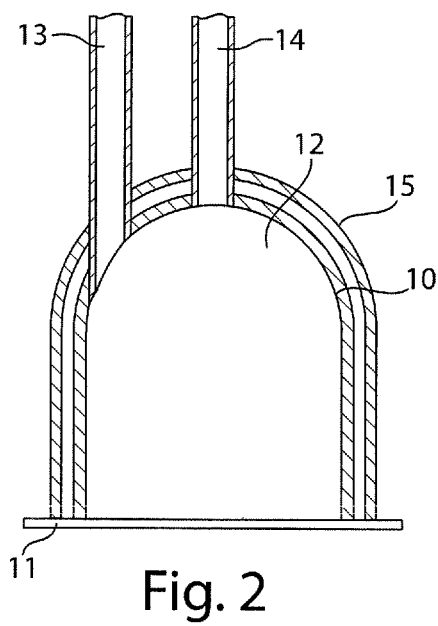
FIG. 2 is a cross sectional view of a acoustic treatment chamber in another illustrative embodiment.

Of course, the arrangement in FIG. 1 is only one illustrative embodiment, and other configurations for the chamber 10 and housing 15 are possible. For example, FIG. 2 shows an arrangement in which the chamber 10 is configured like that in FIG. 1 (with the chamber having a wall with a dome-like shape). However, the housing 15 in this embodiment has a shape that generally conforms to that of the chamber 10 while substantially maintaining an air or other gas gap between the chamber 10 and the housing 15. The air gap need not be particularly large, and although the gap can vary in thickness, in some embodiments may be as thin as about 1 mm, or having an even smaller thickness. Note that the housing 15 and the chamber 10 may contact each other or be effectively attached, e.g., at areas near the optional inlet 13 and outlet 14, while still maintaining a condition in which the chamber wall is substantially surrounded by air or other gas.

The optional inlet 13 and outlet 14 may be arranged in a variety of ways, and in this embodiment the inlet 13 and outlet 14 each include a conduit (such as a flexible tubing) coupled to the chamber 10. The inlet 13 and/or outlet 14 may be provided with fittings (such as quick-connect fittings, luer-type fittings) or other suitable arrangement for making a fluid-tight connection to a sample material supply or receiver. The sample material supply may include, for example, a reservoir of sample material, conduits, pumps, filters, and/or any other suitable components. For example, in one embodiment, the inlet 13 and/or outlet 14 may include a flexible tubing that can interact with a peristaltic pump that causes sample material to flow through the chamber 10. In some embodiments, the inlet and/or outlet may include a check valve, one-way valve, electronically-controlled valves or other arrangement that helps to ensure that flow occurs in a desired way, e.g., so the flow of material is always from the inlet to the outlet even though flow may be intermittent. In some cases, acoustic processing of the sample material may cause the release of gas from the sample material which may interfere with acoustic processing. In this embodiment, the outlet 14 is located at an uppermost portion of the chamber 10 so that any gas in the internal volume 12 may be removed with flow of sample material out of the internal volume 12 and into the outlet 14. However, other arrangements are possible, such as a gas trap, vent, gas scavenger, or other configuration to reduce the presence of gas in the internal volume 12. The inlet 13 and/or outlet 14 (as well as other components including the chamber 10, window 11 and housing 15) may be made sterilizable (e.g., by ethylene oxide, gamma radiation, autoclaving, chemical treatment, etc.) so that a user can be ensured that sample material will not be contaminated. Also, such components can be made and intended for a single use (e.g., as a consumable device), and subsequently discarded or refurbished.

A portion of the chamber 10, such as an upper portion of the chamber 10, may include an inspection window or other arrangement that permits visible light inspection of the internal volume 12. Such inspection may be done by a human, or by a suitably arranged sensor 21 (see FIG. 1) such as a video camera, photodetector, IR detector, and so on. Characteristics of the material in the internal volume 12 detected by the sensor 21 may be used by the controller 20 to control the acoustic energy source 2 or other components of the system 1. For example, if excessive cavitation is to be avoided, the controller 20 may adjust the acoustic energy at the focal zone 17 if the sensor 21 detects the presence of cavitation bubbles of a certain size and/or number. Other features may be detected by the sensor 21, such as the size, density or other characteristics of particles in the chamber 10 in the case where the acoustic treatment is intended to break down the size of particles in the sample material. Thus, the sensor 21 may detect whether acoustic treatment is progressing as desired and whether processing is complete, e.g., to trigger the introduction of additional sample material into the chamber 10. Like the window 11, the inspection window may be formed of any suitable material, such as glass, sapphire, quartz, and/or polymer materials, and/or may be part of the chamber wall. Also, the sensor 21 may be made part of the housing 15 (e.g., attached to a wall of the housing 15) so that when the housing 15 and chamber 10 are placed in service, the sensor 21 may be suitably arranged to detect conditions in the internal volume 12 without any adjustment or other configuration of the sensor 21 being required. A communications and/or power connection of the sensor 21 with the controller 20 may be established wirelessly, or by wire, such as by an electrical connector on the housing 15 contacting a counterpart connector when the housing 15 is mounted to a holder. That is, an acoustic treatment machine that includes the acoustic energy source 2, a container 3 for the coupling medium 4, the controller 20, etc. (e.g., like a Model S2 or Model S220 acoustic treatment machine offered by Covaris, Inc. of Woburn, Mass.) may also include a holder or other mounting arrangement to physically engage with the housing 15 and hold the chamber 10 is a proper position in relation to the coupling medium 4 and/or the acoustic energy source 2. In one embodiment, the holder may include a cylindrical opening that receives a cylindrical portion of the housing 15 and supports the housing 15 in a desired location. The holder and the housing 15 may be fixed relative to each other using a clamp, a set screw, friction fit, or other suitable arrangement.

The body of the chamber 10 may be made of any material or combination of materials suitable to contain the sample in the internal volume 12 during treatment, to act as an environmental seal, and/or to provide an acoustic reflection function. In some embodiments, the chamber 10 may be made of a rigid or flexible material, such as a thermally conductive metal or polymer, or a combination of such materials. Preferably, the material used for the chamber 10 has a low acoustic absorption. In certain embodiments, the upper portion of the chamber 10 (e.g., including an inspection window) can be arranged to reflect acoustic energy back into the internal volume 12 (e.g., functioning with a gas interface), providing additional process efficiencies. If the chamber 10 is made from multiple parts, such as by upper and lower members, the members may be joined together by thermal bonding, adhesive bonding, external clamping, mechanical fasteners with an o-ring or other gasket to form a seal between the members, welding, and so on. If the bond is to be achieved by thermal bonding, the upper and lower members may be made of, or include, film laminates having heat bondable outer layers and heat resistant inner layers.

The internal volume 12 may be sized and shaped as appropriate for the sample material to be treated, e.g., some acoustic treatment applications (such as sterilization) may function more effectively if a relatively small volume of sample material is treated in a relatively small volume, whereas other applications (such as mixing) may produce better results using a larger volume for the internal volume 12. The internal volume 12 can have different shapes or other configuration characteristics, e.g., the internal volume 12 may be defined by vertical walls, can have a conical shape, can have a curved shape, and so on. The chamber 10 can be made of multiple components such as an upper member and lower acoustically transparent member (e.g., window 11), and a body which together define the internal volume that contains the material to be treated. The inner wall of the chamber 10, which defines the internal volume 12, may further include structural elements that have geometries or other features that cause reflected acoustic energy to form secondary focal zones and/or remain substantially within the internal volume 12. Alternately, the chamber 10 and window 11 may be made as a single unitary piece or in other ways.

Figure 3:
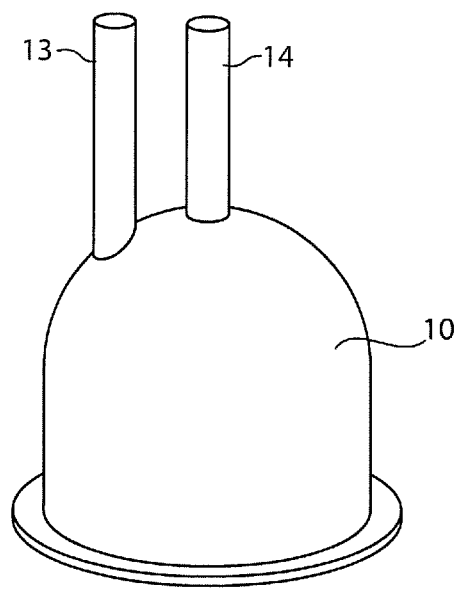
FIG. 3 is a perspective view of the acoustic treatment chamber of FIG. 1.
Figure 4:
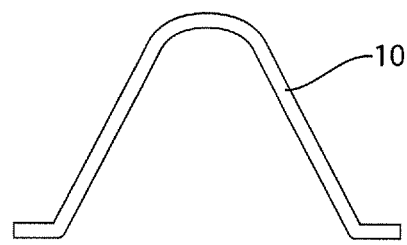
FIG. 4 is a cross sectional view of an acoustic treatment chamber having a dome with a conical shape.
Figure 5:
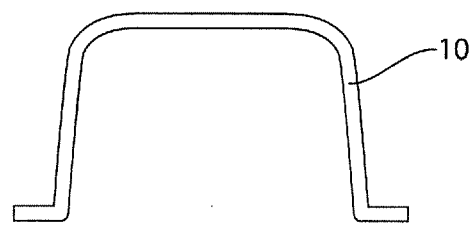
FIG. 5 is a cross sectional view of an acoustic treatment chamber having a dome with a cylindrical shape.
Figure 6:
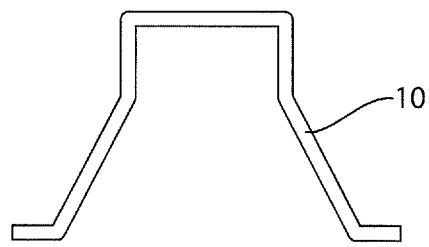
FIG. 6 is a cross sectional view of an acoustic treatment chamber having a dome with a conical and a cylindrical portion.

FIG. 3 shows a perspective view of the dome-shaped chamber 10 of the FIG. 1 embodiment. Although a curved dome shape with a hemispherical upper section has been found to be useful in creating a secondary focal zone, other dome shapes are possible. For example, FIG. 4 shows a cross sectional view of a chamber 10 having a substantially conical shape. Such an arrangement may be useful, for example, for focusing acoustic energy near the top of the chamber 10. FIG. 5 shows another illustrative embodiment in which the chamber 10 has an approximately cylindrical shape. This arrangement may be useful for generating multiple secondary focal zones, e.g., near the periphery of the upper portion of the chamber 10. FIG. 6 shows another illustrative embodiment in which the chamber has a lower portion with a conical shape and an upper portion with a cylindrical shape. This arrangement may help to create a secondary focal zone in a relatively confined area near the top of the chamber 10. Of course, the dome shapes of FIGS. 4-6 could be modified in other ways, e.g., including tetrahedron shapes, oval shapes, geodesic dome shapes, and other regular and irregular arrangements. Although these embodiments are shown without a window 11 or other similar arrangement, a window 11 may be provided at the lower opening of the chamber 10, e.g., by bonding a window 11 to the flange at the lower end of the chamber 10.

As discussed above and shown in FIG. 1, the acoustic treatment system 1 may include a container 3 that contains the acoustic energy source 2, the chamber 10, the coupling medium 4 and/or other components. The container 3 may take any suitable size, shape or other configuration, and may be made of any suitable material or combination of materials (such as metal, plastic, composites, etc.). Although in this illustrative embodiment the container 3 has a can-like configuration with an open top to permit access to the container 3, the container 3 may be arranged to have a lid or other closure. For example, the chamber 10, housing 15, etc., may be received in a hole in a lid that closes the container 3 so that the chamber 10 is suitably positioned at least partially inside the container 3. If the coupling material 4 is solid, the container 3 and the coupling medium 4 may be essentially integrated with each other, with the coupling medium 4 essentially functioning as an acoustic coupling as well as a physical attachment of the acoustic source 2 and the chamber 10 or a holder for the chamber 10.

It should be understood that the chamber 10 may be arranged in any suitable way, and for a variety of different applications. For example, in the embodiment shown in FIG. 1, the inlet 13 and outlet 14 communicate with the internal volume 12 near a top of the volume 12. However, the inlet 13 and outlet 14 may communicate with the internal volume 12 in other ways, e.g., the inlet 13 may be fluidly coupled with the internal volume 12 at a location that is above, or below, of a location where the outlet 14 is fluidly coupled to the internal volume. Having the inlet and outlet coupled at different heights may provide advantages depending on the specific application. For example, in some applications, having the inlet 13 located above the outlet 14 may help control the temperature of the material in the internal volume 12, e.g., cooler fluid entering at the inlet may mix with relatively warm fluid near a top of the internal volume 12. In other applications, having the inlet below the outlet may help ensure that material having a desired size or density is encouraged to exit at the outlet, e.g., larger, more dense particles may remain in the internal volume 12 below the outlet until the particles are broken down by the acoustic treatment into a desired size/density range.

In accordance with another aspect of the invention, the chamber 10 may include one or more elements in the internal volume 12 to help influence the acoustic treatment of the sample material. Such elements may be structural elements and/or may include one or more materials that influence overall acoustic treatment. Structural elements may be disposed loosely within the internal volume 12, may be attached to the chamber or, alternatively, may be integrally formed with the chamber (e.g., the inner wall of the chamber may include appropriately shaped structural elements). For example, one or more elements may be provided in the internal volume 12 to help induce cavitation (e.g., the elements may include suitable nucleation sites for cavitation), help absorb acoustic energy (e.g., to reduce cavitation), help move sample material to desired locations in the internal volume 12 (e.g., one or more baffles may direct sample material to one or more desired locations in the chamber 10), help retain acoustic energy within the internal volume (e.g., one or more structural features, such as ridges with depressions, may serve to partially enclose acoustic energy may limit acoustic energy from exiting the chamber toward the transducer), and so on. The element(s) may be made in a variety of different shapes, sizes and materials, depending on the application or other desired function. For example, the element(s) may include grooves, jagged edges, ridges, protrusions, depressions, steps, partial enclosures, ceramic rods, beads or elements made of other materials, that are positioned in the internal volume 12 and function to provide nucleation sites, to help transfer or otherwise distribute heat in the chamber 10, provide reaction sites or otherwise catalyze or aid in chemical or other reactions in the volume 12, substantially limit transmission of or to trap acoustic energy, generate regions of acoustic energy giving rise to secondary focal zones, direct acoustic energy toward particular locations and other functions. Rods, beads or other structures may be suspended in the internal volume 12, e.g., by a physical support and/or by mixing or other fluid movement in the internal volume caused by the acoustic energy or other material flow. In some embodiments, appropriate structural elements, such as a domed-shaped structure may cause reflected acoustic energy to form one or more secondary focal zones (e.g., highly localized) within the internal volume 12.

The roughness of the surface of the inner wall of the chamber may comprise a structural element where the surface is optionally smooth or rough. For example, the surface of the inner wall may be polished to give rise to a smooth surface; or, the surface may be etched or otherwise treated (e.g., mechanically, chemically, etc.) to result in a roughened surface. In some cases, a smooth surface may result in acoustic energy being readily reflected into a particular direction (e.g., to form a secondary focal zone), while a roughened surface may provide nucleation sites for the formation of multiple smaller secondary focal zones.

In accordance with an aspect of the invention, the acoustic treatment system 1 may be arranged to accommodate continuous acoustic treatment of material in a chamber 10, or multiple chambers 10, for an extended time period, e.g., for 1 hour or more, at a relatively high intensity, e.g., at an output of the acoustic transducer of 200 watts or more, without experiencing excessive heat buildup or other problems. In one embodiment, a piezoelectric transducer functioning as part of the acoustic energy source 2 may operate at an intensity level equal to about 286 watts for several hours in an equilibrium state, i.e., a state in which material is acoustically processed in a chamber 10 without excessive heat build up, transducer burn out or failure, or other conditions that would require stoppage of the acoustic treatment. This is in contrast to prior acoustic treatment arrangements in which continuous acoustic treatment for 1 hour or more could not have been achieved for a variety of different reasons, such as excessive heat buildup, failure of the acoustic source (e.g., due to transducer overheating and subsequent burn out), damage to the sample material, and so on.

Transducer

In certain embodiments, the sonic energy source 2 may include, for example, an ultrasound transducer or other transducer, that produces acoustic waves in the "ultrasonic" frequency range. Ultrasonic waves start at frequencies above those that are audible, typically about 20,000 Hz or 20 kHz, and continue into the region of megahertz (MHz) waves. The speed of sound in water is about 1000 meters per second, and hence the wavelength of a 1000 Hz wave in water is about a meter, typically too long for specific focusing on individual areas less than one centimeter in diameter, although usable in non-focused field situations. At 20 kHz the wavelength is about 5 cm, which is effective in relatively small treatment vessels. Depending on the sample and vessel volume, preferred frequencies may be higher, for example, about 100 kHz, about 1 MHz, or about 10 MHz, with wavelengths, respectively, of approximately 1.0, 0.1, and 0.01 cm. In contrast, for conventional sonication, including sonic welding, frequencies are typically approximately in the tens of kHz, and for imaging, frequencies are more typically about 1 MHz and up to about 20 MHz. In lithotripsy, repetition rates of pulses are fairly slow, being measured in the hertz range, but the sharpness of the pulses generated give an effective pulse wavelength, or in this case, pulse rise time, with frequency content up to about 100 to about 300 MHz, or 0.1-0.3 gigahertz (GHz).

The frequency used in certain embodiments of the invention will also be influenced by the energy absorption characteristics of the sample or of the chamber 10, and/or the characteristics of the gas/chamber wall interface, for a particular frequency. To the extent that a particular frequency is preferentially absorbed or reflected, it may be preferred. The energy can be delivered in the form of short pulses or as a continuous field for a defined length of time. The pulses can be bundled or regularly spaced.

A generally vertically oriented focused ultrasound beam may be generated in several ways by the acoustic energy source 2. For example, a single-element piezoelectric transducer, such as those supplied by Sonic Concepts, Woodinville, Wash., that can be a 1.1 MHz focused single-element transducer, can have a spherical or other curved transmitting surface that is oriented such that the focal axis is vertical. Another embodiment uses a flat unfocused transducer and an acoustic lens (e.g., the window 11 or other element) to focus the beam. Still another embodiment uses a multi-element transducer such as an annular array in conjunction with focusing electronics to create the focused beam. The annular array potentially can reduce acoustic sidelobes near the focal point by means of electronic apodizing, that is by reducing the acoustic energy intensity, either electronically or mechanically, at the periphery of the transducer. This result can be achieved mechanically by partially blocking the sound around the edges of a transducer or by reducing the power to the outside elements of a multi-element transducer. This reduces sidelobes near the energy focus, and can be useful to reduce heating of the chamber 10. Alternatively, an array of small transducers can be synchronized to create a converging beam. Still another embodiment combines an unfocused transducer with a focusing acoustic mirror to create the focused beam. This embodiment can be advantageous at lower frequencies when the wavelengths are large relative to the size of the transducer. The axis of the transducer of this embodiment can be horizontal and a shaped acoustic mirror used to reflect the acoustic energy vertically and focus the energy into a converging beam.

In certain embodiments, the focal zone can be small relative to the dimensions of the treatment chamber 10 to avoid heating of the treatment chamber 10. In one embodiment, the focal zone has a width of approximately 1 mm. The focal zone may have a width of less than about 2 cm, for example, between 0.1 to 10 mm. Heating of the treatment chamber 10 can be reduced by minimizing acoustic sidelobes near the focal zone. Sidelobes are regions of high acoustic intensity around the focal point formed by constructive interference of consecutive wavefronts. The sidelobes can be reduced by apodizing the transducer either electronically, by operating the outer elements of a multi-element transducer at a lower power, or mechanically, by partially blocking the acoustic waves around the periphery of a single element transducer. Sidelobes may also be reduced by using short bursts, for example in the range of about 3 to about 5 cycles in the treatment protocol.

The transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing. The response is linear if not overdriven. The high-energy focus zone 17 of one of these domes is typically cigar-shaped. At 1 MHz, the focal zone 17 is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone 17, defined as having an acoustic intensity within about 6 dB of the peak acoustic intensity, is formed around the geometric focal point.

The wavelength, or characteristic rise time multiplied by sound velocity for a shock wave, is in the same general size range as a biological cell, for example about 10 to about 40 microns. This effective wavelength can be varied by selection of the pulse time and amplitude, by the degree of focusing maintained through the interfaces between the source and the material to be treated, and the like.

Another source of focused acoustic pressure waves is an electromagnetic transducer and a parabolic concentrator, as is used in lithotripsy. The excitation of such devices tends to be more energetic, with similar or larger focal regions. Strong focal peak negative pressures of about −16 MPa have been observed. Peak negative pressures of this magnitude provide a source of cavitation bubbles in water, which can be desirable in an extraction process.

Drive Electronics and Waveform Control.

One treatment protocol for treating material with acoustic energy in the chamber 10 can include variable acoustic waveforms combined with sample motion and positioning to achieve a desired effect. The acoustic waveform of the transducer may have many effects, including: acoustic microstreaming in and near cells due to cavitation, that is flow induced by, for example, collapse of cavitation bubbles; shock waves due to nonlinear characteristics of the fluid bath; shock waves due to cavitation bubbles; thermal effects, which lead to heating of the sample, heating of the sample vessel, and/or convective heat transfer due to acoustic streaming; flow effects, causing deflection of sample material from the focal zone due to shear and acoustic pressure, as well as mixing due to acoustic streaming, that is flow induced by acoustic pressure; and chemical effects. The waveform of focused sound waves can be a single shock wave pulse, a series of individual shock wave pulses, a series of shock wave bursts of several cycles each, or a continuous waveform. Incident waveforms can be focused directly by either a single element, such as a focused ceramic piezoelectric ultrasonic transducer, or by an array of elements with their paths converging to a focus. Alternatively, multiple foci can be produced to provide ultrasonic treatment to multiple treatment zones, vessels, or wells. Additionally, the flow of the sample material into, or out of the processing chamber 10 can interact with the acoustic effects, and the acoustic streaming can be modified to enhance this sample flow in a desirable manner.

The treatment protocol can be optimized to maximize energy transfer while minimizing thermal and flow effects. The treatment protocol also can effectively mix the contents of the treatment chamber 10, in the case of a particulate sample suspended in a liquid. Energy transfer into the sample can be controlled by adjusting the parameters of the acoustic wave such as frequency, amplitude, and cycles per burst. Temperature rise in the sample can be controlled by limiting the duty cycle of the treatment and by optimizing heat transfer between the treatment chamber 10 and the coupling medium 4. Heat transfer can be enhanced by promoting forced convection by acoustic streaming in the chamber 10 and in the fluid bath in the proximity of the chamber 10.

For example, for a cellular disruption and extraction treatment, an example of an effective energy waveform is a high amplitude sine wave of about 1000 cycles followed by a dead time of about 9000 cycles, which is about a 10% duty cycle, at a frequency of about 1.1 MHz. The sine wave electrical input to the transducer typically results in a sine wave acoustic output from the transducer. As the focused sine waves converge at the focal point, they can become a series of shock waves due to the nonlinear acoustic properties of the water or other fluid in the coupling medium 4. This protocol treats the material in the focal zone effectively during the "on" time. As the material is treated, it is expelled from the focal zone and new material circulates into the focal zone. The acoustic "on" and "off" times can be cycled to be effective, for example, for extracting the cellular contents of ground or particulate leaf tissue, while causing minimal temperature rise in the treatment vessel.

Further advantage in disruption and other processes may be gained by creating a high power "treat" interval alternating with a low power "mix" interval. More particularly, in this example, the "treat" interval utilizes a sine wave that has a treatment frequency, a treatment cycles-per-burst count, and a treatment peak-to-peak amplitude. The "mix" interval has a mix frequency, a mix cycles-per-burst count and a lower mix peak-to-peak amplitude. Following each of the intervals is a dead time. Of course, these relationships are merely one example of many, where one interval in considered to be high power and one interval is considered to be low power, and these variables and others can be altered to produce more or less energetic situations. Additionally, the treat function or interval and the mix function or interval could emit from different or multiple transducers in the same apparatus, optionally emitting at different frequencies.

High power/low power interval treatments can allow multiple operations to be performed, such as altering permeability of components, such as cells, within the sample followed by subsequent mixing of the sample. The treat interval can maximize cavitation and bioeffects, while the mix interval can maximize mixing within the treatment vessel and/or generate minimal heat. Adding a longer, high power "super-mix" interval occasionally to stir up particles that are trapped around the periphery of the chamber 10 can provide further benefits. This "super-mix" interval generates additional heat, so it is programmed to treat infrequently during the process, for example, every few seconds. Additionally, dead times between the mix and treat intervals, during which time substantially no energy is emitted from the sonic energy source, can allow fresh material to circulate into the energy focal zone of the target.

The waveform of the sound wave typically is selected for the particular material being treated. For example, to enhance cavitation, it can be desirable to increase the peak negative pressure following the peak positive pressure. For other applications, it can be desirable to reduce cavitation, but maintain the peak positive pressure. This result can be achieved by performing the process in a pressurized chamber 10 at a slight pressure above ambient. For example, if the waveform generated has a peak negative pressure of about −5 MPa at the focal zone 17, then the entire chamber may be pressurized to about 10 MPa to eliminate cavitation from occurring during the process. Material to be treated can be pressurized on a batch or a continuous basis within the internal volume 12 of the chamber 10. That is, a volume of material may be delivered into the internal volume 12, treated acoustically while material flow is stopped, and then a new volume of material may be delivered into the internal volume 12 once treatment of the initial volume is complete.

Typically, the shock wave at the focal zone 17 is characterized by a rapid shock front with a positive peak pressure in the range of about 15 MPa, and a negative peak pressure in the range of about negative 5 MPa. This waveform is of about a few microseconds duration, such as about 5 microseconds. If the negative peak is greater than about 1 MPa, cavitation bubbles may form. Cavitation bubble formation also is dependent upon the surrounding medium. For example, glycerol is a cavitation inhibitive medium, whereas liquid water is a cavitation promotive medium. The collapse of cavitation bubbles forms "microjets" and turbulence that impinge on the surrounding material.

Control of the acoustic energy source 2 may be performed by the controller 20 using a feedback control mechanism so that any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wave train pattern, and position), can enhance performance of the treatment system 1. A variety of sensors or sensed properties may be used by the controller 20 for providing input for feedback control. These properties can include sensing of temperature of the sample material; sonic beam intensity; pressure; coupling medium properties including temperature, salinity, and polarity; sample material position; conductivity, impedance, inductance, and/or the magnetic equivalents of these properties, and optical or visual properties of the sample material. These optical properties, which may be detected by the sensor 21 typically in the visible, IR, and UV ranges, may include apparent color, emission, absorption, fluorescence, phosphorescence, scattering, particle size, laser/Doppler fluid and particle velocities, and effective viscosity. Sample integrity or comminution can be sensed with a pattern analysis of an optical signal from the sensor 21. Particle size, solubility level, physical uniformity and the form of particles could all be measured using instrumentation either fully stand alone sampling of the fluid and providing a feedback signal, or integrated directly with the focused acoustical system via measurement interface points such as an optical window, Any sensed property or combination thereof can serve as input into a control system. The feedback can be used to control any output of the system, for example beam properties, sample position or flow in the chamber 10, treatment duration, and losses of energy at boundaries and in transit via reflection, dispersion, diffraction, absorption, dephasing and detuning.

According to certain embodiments of the present invention, several aspects of the treatment system 1 can enhance the reproducibility and/or effectiveness of particular treatments using ultrasonic energy in in vitro applications, where reproducibility, uniformity, and precise control are desired. These aspects include the use of feedback, precise focusing of the ultrasonic energy, monitoring and regulating of the acoustic waveform (including frequency, amplitude, duty cycle, and cycles per burst), positioning of the chamber 10 relative to the ultrasonic energy so that the sample material is uniformly treated, controlling movement or flow of the sample relative to the focus of ultrasonic energy during a processing step, and/or controlling the temperature of the sample being treated, either by the ultrasonic energy parameters or through the use of temperature control devices such as a water bath. A treatment protocol can be optimized, using one or a combination of the above variables, to maximize, for example, shearing, extraction, permeabilization, comminution, stirring, or other process steps, while minimizing undesirable thermal effects.

In one embodiment of the invention, high intensity ultrasonic energy is focused on a chamber 10, and "real time" feedback relating to one or more process variables is used to control the process. In another embodiment, the process is automated and is used in a high throughput system, such as a continuous flowing stream of material to be treated, optionally segmented.

In certain embodiments, the processing system can include a high intensity transducer that produces acoustic energy when driven by an electrical or optical energy input; a device or system for controlling excitation of the transducer, such as an arbitrary waveform generator, an RF amplifier, and a matching network for controlling parameters such as time, intensity, and duty cycle of the ultrasonic energy; a system or method for transferring material into and out of the process zone, either actively or passively, to allow automation and the implementation of feedback from monitoring; a temperature sensor; a device for controlling temperature; one or more reaction chambers 10; and a sensor for detecting, for example, optical, radiative, and/or acoustic signatures. The feedback signal can also come from a signal provided by either external or integrated measurement methods such as particle size, solubility, and form factors.

Additional aspects of the invention relate to material flow circuit arrangements for acoustically treating the material. For example, in some embodiments the sample material can be transferred to/from one or more chambers 10 through passive or active means, such as direct pumping methods or passive gravity driven methods.

Figure 7:
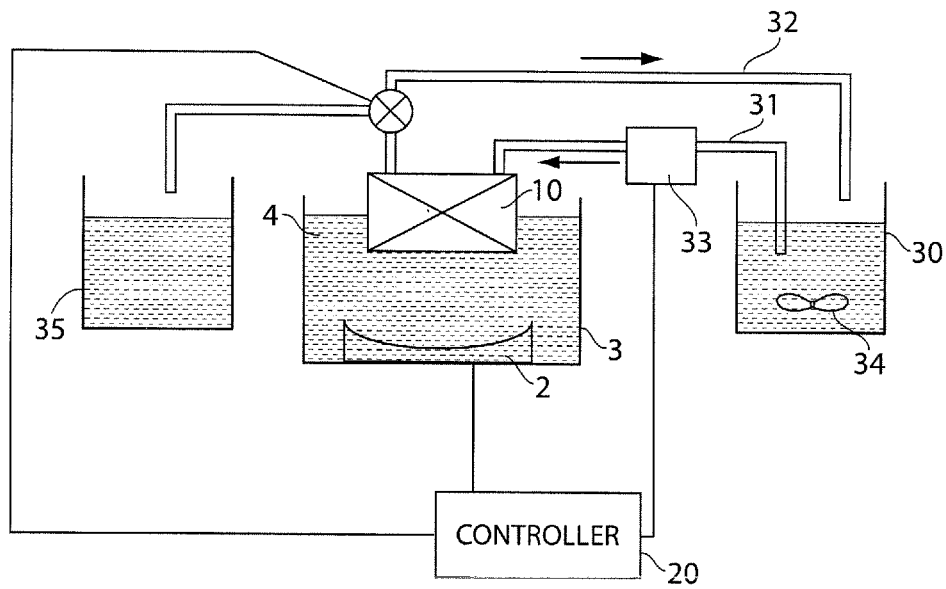
FIG. 7 is an illustrative embodiment of an acoustic treatment system including a reservoir with an agitator.

In one illustrative embodiment shown schematically in FIG. 7, an acoustic treatment system 1 may include one or more treatment chambers 10 that is fluidly coupled to a reservoir 30 that holds material to be treated in the chamber 10. In this illustrative embodiment, the inlet 13 of the chamber 10 is fluidly coupled to a supply conduit 31 and the outlet 14 of the chamber 10 is fluidly coupled to a return conduit 32. As discussed above, the supply and return conduit 31, 32 may include flexible tubing suitable for interaction with a peristaltic pump or other arrangement, and may be included with the chamber 10 as part of a disposable or resposable device. Thus, material in the reservoir 30 may be circulated through the chamber 10 at any suitable flow rate, pressure, time or other parameter so that the material is suitably processed by acoustic energy in the chamber 10. Flow of the material may be caused by gravity, by acoustic streaming (e.g., in the chamber 10), by a pump 33 (such as a syringe pump, a peristaltic pump, a gear pump, and so on), or other motive force. In some embodiments, a pressure may be maintained in the chamber 10 (and/or in the reservoir 30) by applying a pressurized gas, a pump or other component to generate the desired pressure in the desired locations. As discussed above, pressurizing the material in the chamber 10 and/or elsewhere may help reduce cavitation, enhance reaction rates, and/or have other desired affects.

In one aspect of the invention, the reservoir 30 may include an agitator 34, such as a mixing blade, stirrer, homogenizer or other device that functions to mechanically mix, shear or otherwise cause movement of the material in the reservoir 30. Movement of the material may have desired affects, such as pretreating the material prior to acoustic treatment, maintaining a desired distribution of material components throughout the volume in the reservoir, and so on. An arrangement like that in FIG. 7 may allow the system 1 to repeatedly expose the sample material to acoustic treatment so that the material has desired properties when treatment is complete. The acoustic treatment conditions in the chamber 10 may remain constant, or nearly constant throughout the process, or the conditions may change over time. For example, the material may initially include relatively large particles of a substance to be broken down into smaller particles and ultimately solubilized in a carrier liquid. Initial acoustic treatment conditions (as well as operation of the agitator 34) may be favorable to break the large particles down into smaller particles. After some initial treatment, the large particles may be broken down, and the acoustic treatment conditions (and the operation of the agitator 34) may be adjusted to enhance the speed and effectiveness of putting components of the small particles into solution. Adjustments to the treatment conditions may be made based on any suitable criteria, such as sensed material properties (such as particle size, density, etc.), a time elapsed, user input, and so on. The system 1 may optionally include a second reservoir 35 that receives material when processing of the material is determined to be complete (again, which determination may be made based on detected material properties, elapsed time, etc.). In this embodiment, the return conduit 32 includes a three-way valve 36 (or other suitable arrangement) that permits the controller 20 to direct material to the second reservoir 35 as desired. Of course, other flow control arrangements may be used, and control of material flow to the second reservoir 35 may be based on sensed parameters, such as elapsed processing time, detected particle sizes or density, material color or other optical properties, or other characteristics of the sample material.

Figure 8:
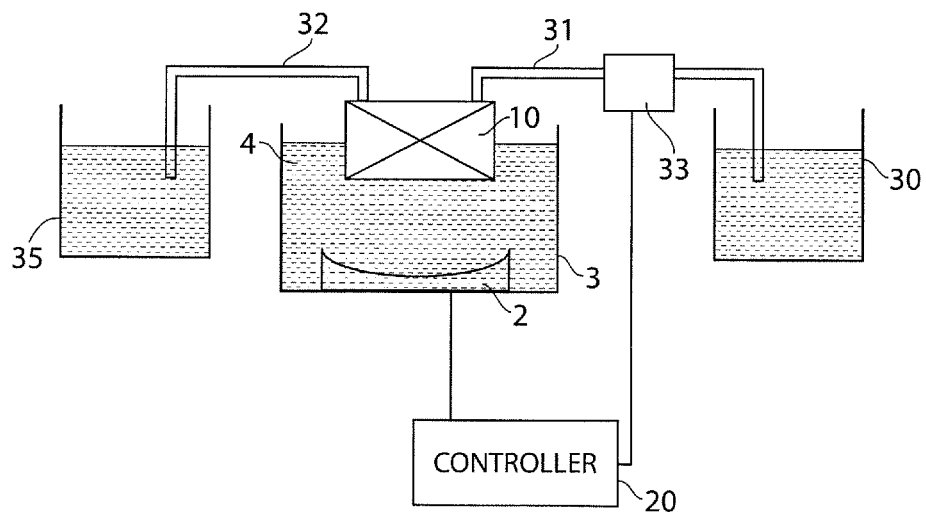
FIG. 8 is an illustrative embodiment of an acoustic treatment system arranged for oscillating flow of material.

FIG. 8 shows another illustrative embodiment for an acoustic treatment system 1 that includes a first reservoir 30 fluidly coupled to a chamber 10 via a supply conduit 31, and a second reservoir 35 fluidly coupled to the chamber 10 via a return conduit 32. In this embodiment, material in the first reservoir 30 may flow through the chamber 10 for acoustic treatment, and thereafter be deposited in the second reservoir 35. In the case that subsequent acoustic treatment is desired, the material may be again caused to flow through the chamber 10, albeit in the opposite direction and into the first reservoir 30 after a second treatment. Flow of the material may be caused in any suitable way, such as by a pump 33, by acoustic streaming in the chamber 10, by gravity (e.g., by establishing the level of material in one reservoir to be higher than the other, causing a siphon to be created for flow), or others. The chamber 10 and/or the conduits 31, 32 may include one or more windows, sensors or other components suitable to detect properties of the sample material. These detected features may be used to control various parameters of the system 1, such as flow rate, pressure, acoustic treatment characteristics, and so on.

Figure 9:
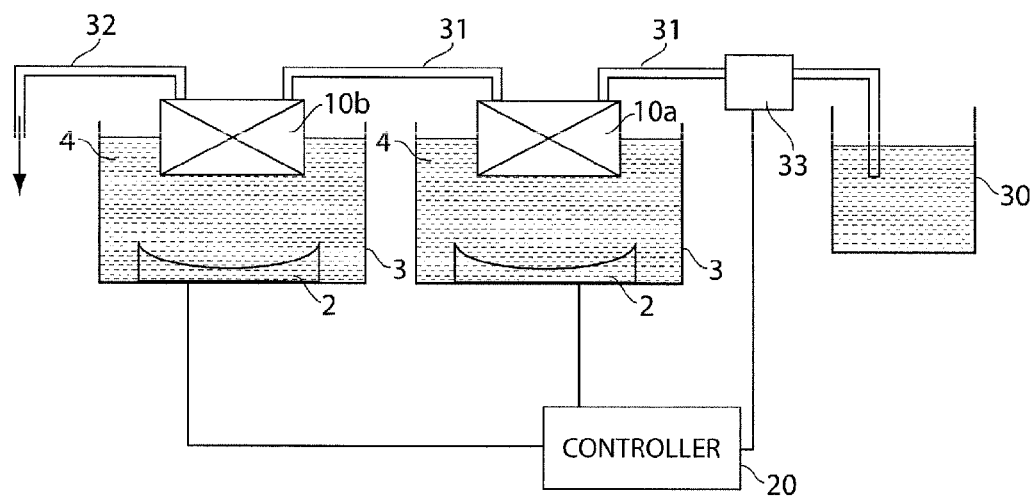
FIG. 9 is an illustrative embodiment of an acoustic treatment system arranged for serial treatment of material using multiple treatment chambers.

In another illustrative embodiment, an acoustic treatment system 1 may include two or more treatment chambers 10 that are arranged in serial fashion. For example, FIG. 9 shows an embodiment in which two chambers 10 are in fluid communication with each other and a reservoir 30. The first chamber 10a may be used to apply a 'pretreatment' or other first treatment to the sample material, while the second chamber 10b applies a 'finishing" or other second treatment to the material. The acoustic energy and other treatment parameters may be set and controlled independently at each chamber 10 to optimize the overall processing goals. For example, the sample material can first pass through a 'roughing' stage in the first chamber 10a to break up large chunks/clumping in the sample material (e.g., where the treatment conditions provide a general, high level mixing and homogenization of the sample) before the material passes to the next stage (e.g., a 'finishing' stage) for additional acoustic treatment that refines the ultimate properties of the material, such as by extracting desired materials, solubilizing components in the material, and so on. As many stages, i.e., chambers 10, as is necessary may be used in a system 1 like that in FIG. 9 to achieve the desired output.

Aspects of the invention also relate to methods for acoustically treating material using the various systems 1 described above. For example, one method in accordance with the invention involves treating a material using a system like that in FIG. 7 wherein material is agitated by an agitator in a reservoir, the material is caused to flow from the reservoir into a chamber 10, the material is exposed to focused acoustic energy in the internal volume of the chamber 10 (where the acoustic energy at a focal zone has the properties described herein), and the material is caused to flow back to the reservoir. Optionally, a processing state of the material may be detected, e.g., while the material is in the chamber 10 or return conduit, and if the material is suitably processed, the material may be caused to flow to an other reservoir. Relatively large volumes of material, such as 1 gallon, 10 gallons, 100 gallons, 1000 gallons or more of material may be held in the reservoir and caused to flow in a circulatory manner through one or more chambers 10 in a continuous fashion. Thus, the treatment method may be continuously performed for 1 hour or more, with the acoustic energy source continuously operating at a power output equivalent to 200 watts or more.

Another method in accordance with the invention relates to treating material using a system like that in FIG. 8 or a similar system. For example, material may be caused to flow in a first direction into a chamber 10, the material is exposed to focused acoustic energy in the internal volume of the chamber 10 (where the acoustic energy at a focal zone has the properties described herein), and the material is caused to flow out of the chamber 10. Thereafter, the material may be caused to flow in a second direction opposite to the first direction into the chamber 10, where the material is again acoustically treated, and flows in the second direction out of the chamber 10. Flow may be caused by one or more pumps, acoustic streaming, gravity and/or other motive forces. Also, acoustic treatment may be performed in a continuous manner, for extended periods of time (over 1 hour) with the acoustic energy source 2 operation at a power output of 200 watts or greater. As with other methods in accordance with the invention, various aspects may be combined together, such as chambers that include acoustic windows, chambers that include heat exchanger features, and so on.

Another method in accordance with the invention relates to treating material using a system like that in FIG. 9 or a similar system. For example, material may be caused to flow into a first chamber 10, the material is exposed to focused acoustic energy in the internal volume of the first chamber 10 (where the acoustic energy at a focal zone has the properties described herein), and the material is caused to flow out of the first chamber 10, and into a second chamber 10, where the material is again acoustically treated. Serial treatment of the material may be repeated with three or more chambers, and the treatment conditions may be the same, or different, in the different chambers 10. Acoustic treatment may be performed in a continuous manner, for extended periods of time (over 1 hour) with the acoustic energy source 2 operation at a power output of 200 watts or greater. As with other methods in accordance with the invention, various aspects may be combined together, such as chambers that include acoustic windows, chambers that include heat exchanger features, and so on.

Figure 10:
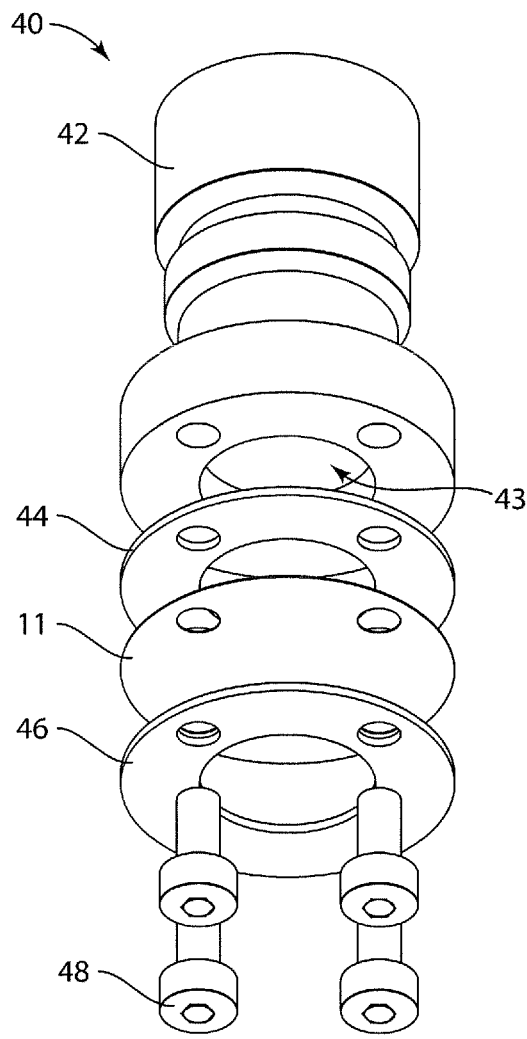
FIG. 10 is an exploded perspective view of an acoustic treatment system in accordance with some embodiments.

FIG. 10 shows an exploded perspective view of various parts of an embodiment of a processing apparatus 40. A lower portion of the chamber body 42 includes a wall having an inner surface that defines the internal volume 43 of the chamber. In this embodiment, the internal volume 43 is cylindrical in shape with a substantially flat upper region and having a width that is greater than the depth. Optionally disposed on the lowermost surface of the body 42 is a gasket 44 which may have an appropriate thickness (e.g., 0.001-0.1 inches, 0.010 inches, etc) and may include any suitable material. For example, the gasket may include silicone, an elastomeric material or another material that provides a suitable sealing function so that fully enclosed sample material does not leak from the internal volume 43. The gasket 44 may include an opening so as not to obstruct entry of acoustic energy into the internal volume 43. As discussed previously, a window 11 may be positioned over the gasket 44 that may enclose the sample within the internal volume 43 as well as appropriately transmit, or may be acoustically transparent to, acoustic energy having a frequency of between 100 kHz and 100 MHz. The window 11 may be appropriately secured to the chamber body 42 by a window frame 46 and fasteners 48.

Processing chambers in accordance with the present disclosure are not limited to the features depicted in FIG. 10. For instance, the gasket 44, window frame 46 and fasteners 48 are only intended to show an example of a suitable manner in which the window 11 may be appropriately positioned adjacent to the internal volume 43. In other embodiments, a crimp cap (e.g., made of a malleable material such as aluminum) is used to affix the window 11 to the body 42 adjacent to the internal volume 43.

In some embodiments, processing apparatuses having appropriate chambers are manufactured as single-use consumable apparatuses. In such arrangements, sample material is deposited into the internal volume of the chamber, a window appropriate for transmitting acoustic energy is positioned so as to enclose the sample material within the internal volume of the chamber, and an acoustic source is used to acoustically treat the sample. After a desired amount of processing, the window may be removed and the sample material is collected. After collection of the sample material, the processing chamber may be discarded. Alternatively, in some cases, processing chambers may be provided as multiple-use apparatuses. That is, once sample material is processed, the chamber may be used again after appropriate handling (e.g., cleaning, sterilizing, refurbishing, retooling).

Figure 11:
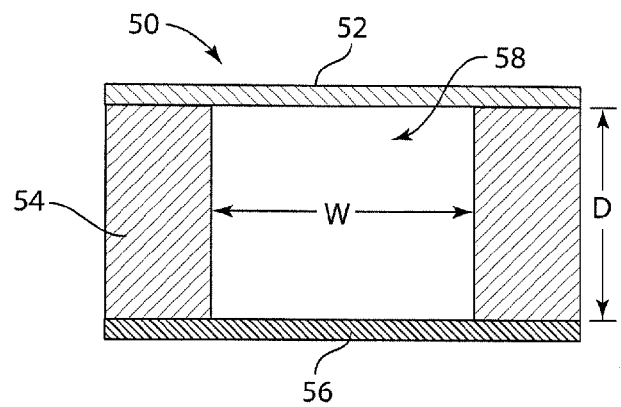
FIG. 11 is a cross sectional schematic of an illustrative embodiment of an acoustic treatment chamber.
Figure 12:
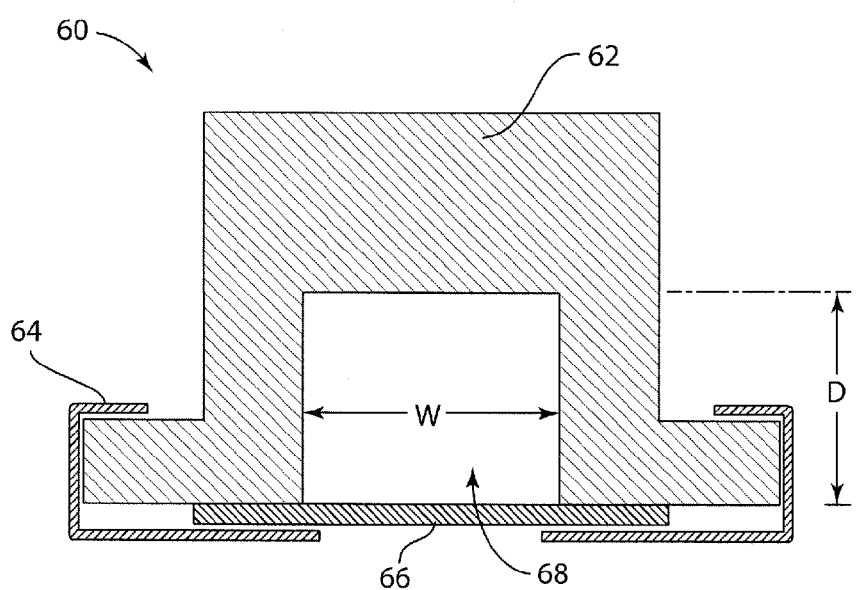
FIG. 12 is a cross sectional schematic of another illustrative embodiment of an acoustic treatment chamber.

FIGS. 11 and 12 depict cross sectional schematics of different embodiments of cylindrical chambers 50, 60, each of which may be suitably incorporated into embodiments of a processing apparatus such as that shown in FIG. 10. Although not a requirement for embodiments of the present disclosure, the cylindrical chambers 50, 60 both have a substantially flat upper surface.

In the embodiment of FIG. 11, the chamber 50 includes upper wall 52 and side wall 54 formed of different materials; although, in some embodiments, upper and side walls 52, 54 may be formed of the same material, similar to that shown in FIG. 12. Although the inner surface of the chamber 50 is illustrated to be smooth, it can be appreciated that the walls 52, 54 may incorporate any suitable arrangement of structural elements in accordance with embodiments described herein. A window 56 is affixed to the bottom surface of the side wall 54, defining an internal volume 58 and providing a final enclosure to the sample held within the chamber. The window may be affixed to the bottom surface of the side wall 54 by any suitable method, such as through an adhesive bond or the adherence of a crimp cap. The internal volume 58 has a depth D and a width W which may provide an appropriate geometric structure for acoustic reflections to form secondary focal zones.

The embodiment of FIG. 12 involves a chamber 60 having a body 62 which includes both the upper wall and the side wall of the chamber formed integrally as a single material. The window 66 is positioned on the bottom surface of the body 62 so as to define the internal volume 68 which, in turn, has a depth D and a width W, which also may provide for a particular geometry for acoustic reflections to form secondary focal zones. As shown, the window 66 may be affixed to the body 62 with a cap 64, such as one that crimps around the window to provide a suitable attachment (e.g., a malleable aluminum crimp cap).

The specific dimensions of the internal volume of the chamber may be designed so as to give rise to secondary focal zones that enhance certain results, such as the efficiency of acoustic processing. For instance, an internal volume of a chamber may have a width (e.g., diameter) W of approximately 11 mm and a depth of approximately 3 mm, giving rise to a volume of about 300 μL. An internal volume of a chamber may also have a width W of approximately 10 mm and a depth of approximately 6 mm, giving rise to a volume of about 500 μL. When operated to process samples with focused acoustic energy having a frequency of about 0.5 MHz, in some cases, the 300 μL chamber may give rise to a processing efficiency that is greater than that produced using the 500 μL chamber. For example, processing a sample in the 300 μL chamber may require less power (e.g., 5-10 times less power) than processing the sample in the 500 μL chamber at similar conditions to achieve a substantially similar result.

The inventors recognize and appreciate the empirical nature of focused acoustic processing and that the effects of such processing can be enhanced when a chamber having a particular geometry and/or incorporating structural elements is used, for example, due to various effects such as tuning, resonance, focal zone placement, etc. In some cases, a chamber shaped in a particular manner may be conducive to reaching a state of resonance when a sample held within the chamber is exposed to focused acoustic energy having a suitable frequency range. When resonance of acoustic energy is achieved within the internal volume of a chamber, the acoustic processing effects may be enhanced significantly (e.g., may be more efficient).

Various embodiments where acoustically reflective chambers are used to treat samples with focused acoustic energy have been found to produce surprising results where acoustic processing is more effective and/or more efficient than previous arrangements where non-reflective chambers are used. For example, in a series of particle micronization experiments, focused acoustic treatment using chambers such as those illustrated in FIGS. 11 and 12 produce nano-suspensions having a much lower average particle size and a tighter distribution of polydispersity index than that observed using a conventional test tube. Such observations indicate the unexpected effect where chambers having particular characteristics (e.g., structural geometry, reflective nature, material properties, or other features) may be advantageous for use in focused acoustic processing of sample material. Accordingly, favorable processing conditions may arise due to the formation of one or more secondary focal zones in a chamber and/or limiting the amount of acoustic energy that travels back toward the transducer.

Figure 13:
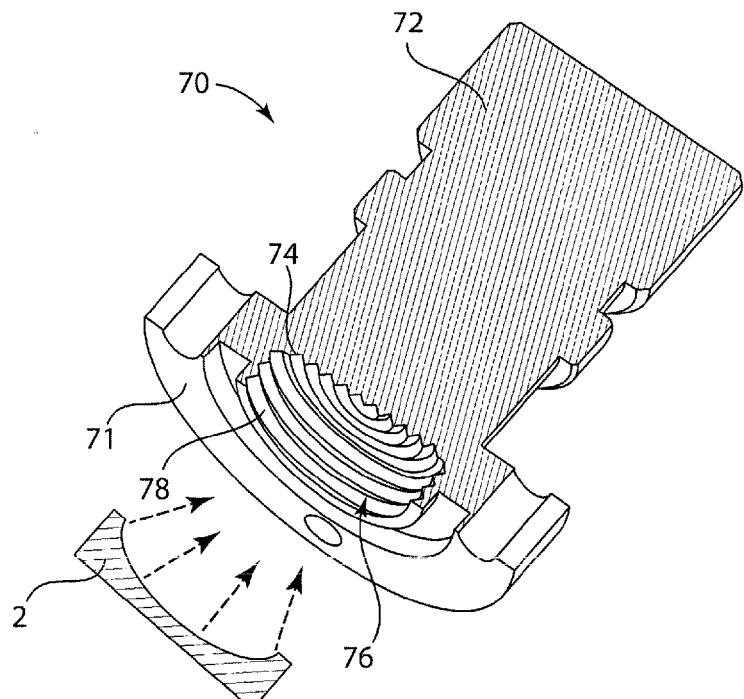
FIG. 13 is a cutaway perspective view of an illustrative embodiment of an acoustic treatment chamber having an inner wall with various structural elements.

FIG. 13 shows a perspective cutaway of an embodiment of an acoustic treatment device 70 having a body 72 and chamber 74 with a wall defining an internal volume 76. In this embodiment, the body 72 is composed of stainless steel which provides an acoustically reflective surface at the inner wall of the chamber 74. The chamber 74 has a generally cylindrical shape and has a number of structural elements 78 integrally disposed along the inner side and upper walls of the chamber. FIG. 13 also shows schematically the location of the transducer 2 and the acoustic energy generated by the transducer (given by dashed arrows) in relation to the chamber. Such an arrangement may help to reflect acoustic energy within the internal volume 76 so as to create one or more secondary focal zones in the sample material and for the acoustic energy to remain, to a large extent, within the internal volume 76. The reflected acoustic energy may be directed in a manner that creates secondary focal zones for further processing of the sample material while also being urged in a direction away from the transducer.

Accordingly, an insubstantial amount of reflected acoustic energy travels back toward the transducer, as acoustic reflections back into the transducer might result in damage to the transducer, or might cause the transducer to shut down (e.g., triggered by electronic protection circuitry). In such cases, any acoustic energy that is reflected back into the transducer is insufficient to cause damage to the transducer or to result in shut down of the transducer. While the surface of the inner wall is acoustically reflective (e.g., by virtue of the inner wall comprising an acoustically reflective material, or an interface that is acoustically reflective), the structural elements may serve to maintain the reflected acoustic energy within a close proximity of the surface of the inner wall, thus, limiting transmission of acoustic energy back out of the internal volume 76.

The structural elements shown in FIG. 13 include grooves comprising jagged-edged ridges and troughs that run along the side wall of the chamber which are also concentrically arranged along the upper wall of the chamber. Though, structural elements of the chamber may be shaped or arranged in any suitable manner. For example, structural elements may include protrusions and/or depressions arranged in a grid-like, or checkerboard configuration along the side and upper walls of the chamber. Structural elements disposed along the inner wall of the chamber may include a stepped arrangement, giving rise to a pyramidal or conical shape of the chamber. Structural elements may be provided in other ways, e.g., including tetrahedron shapes, arcuate shapes, and other regular and irregular arrangements. Although the chamber of FIG. 13 is not shown with a window or other similar arrangement, a window may be provided at the lower opening of the chamber 70, such as by positioning a window against the flange 71 at the lower end of the chamber 70 (e.g., using an adhesive bond, crimp cap, etc.).

Figure 14:
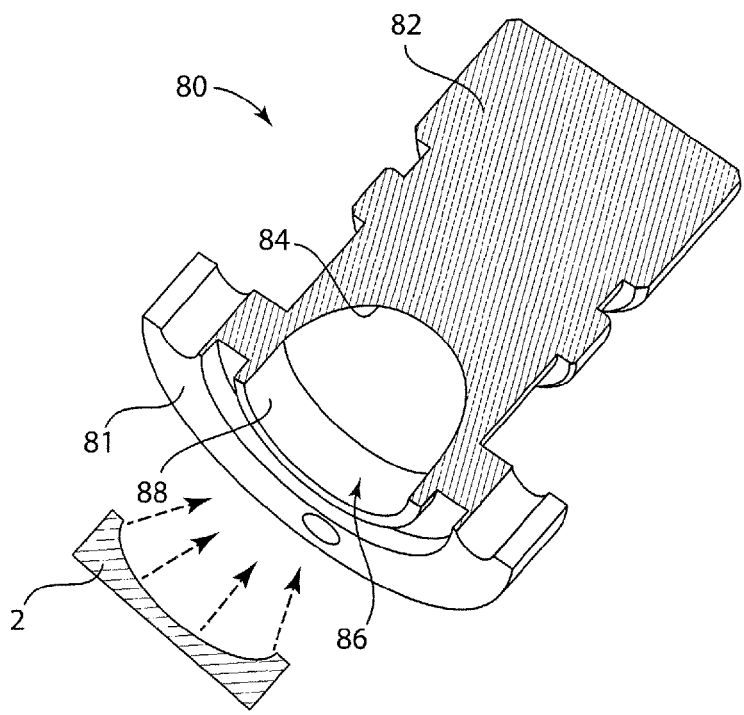
FIG. 14 is a cutaway perspective view of an illustrative embodiment of an acoustic treatment chamber having a dome.

FIG. 14 depicts an embodiment of an acoustic treatment device 80 having a body 82 and chamber 84 having a wall defining an internal volume 86. In this embodiment, the body 82 is comprised of stainless steel so that the inner wall is acoustically reflective and the chamber 84 is dome shaped, having a generally smooth surface 88. The location of the transducer 2 and the acoustic energy generated by the transducer (given by dashed arrows) in relation to the chamber is also schematically illustrated. This arrangement may result in focused acoustic energy within the internal volume 86 reaching the surface of the inner wall to be reflected back so as to form one or more secondary focal zones in the sample material. The reflected acoustic energy may be largely retained within the internal volume 86 of the chamber with an insubstantial amount of acoustic energy, if any, being transmitted back toward the transducer. In some cases, the reflected acoustic energy may be directed generally away from the transducer. Similar to that described above, any acoustic energy reflected back into the transducer is insufficient to cause damage to the transducer or to result in the transducer to shut down.

As discussed further above particularly with respect to FIGS. 2-6, the dome shaped chamber may be shaped according to any suitable arrangement, for example, the chamber may be substantially conical or cylindrical in shape. In some embodiments, structural elements, such as grooves, protrusions and depressions with jagged or smoothed edges may be provided along the inner wall of the chamber, also giving rise to the formation of one or more secondary focal zones. Similarly to that described above for FIG. 13, a window may be provided at the lower opening of the chamber 80, for example, by suitably placing a window against the flange 81 at the lower end of the chamber 70.

Figure 15:
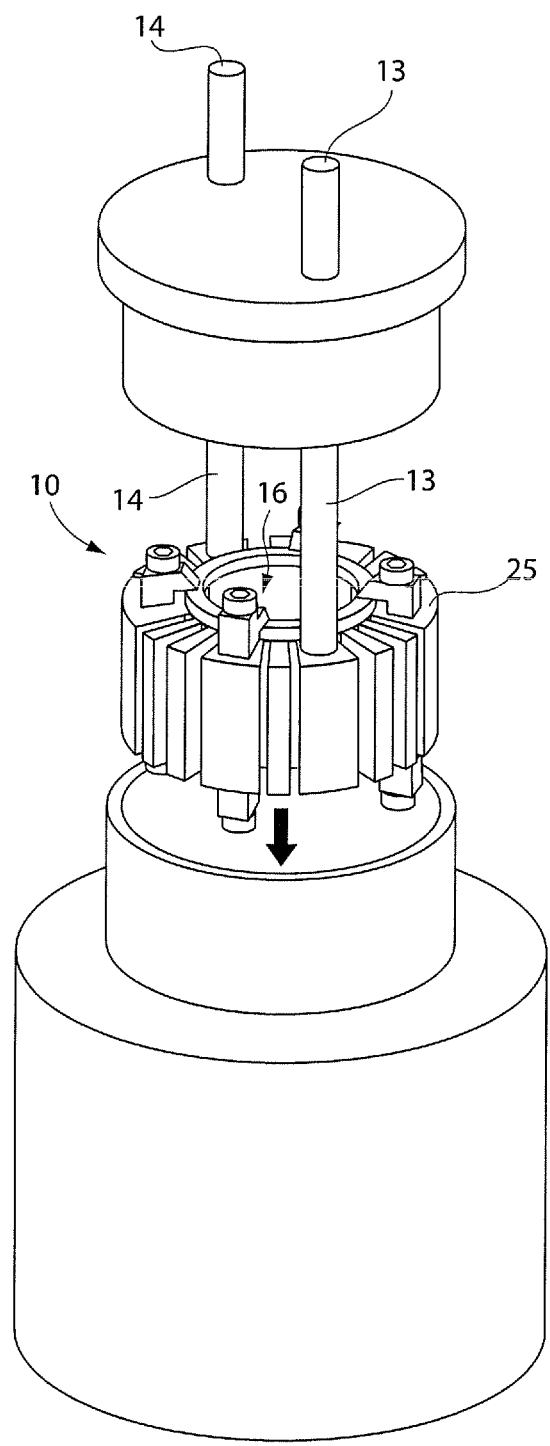
FIG. 15 is an exploded perspective view of an acoustic treatment system in an embodiment including a chamber that is received in a vessel.
Figure 16:
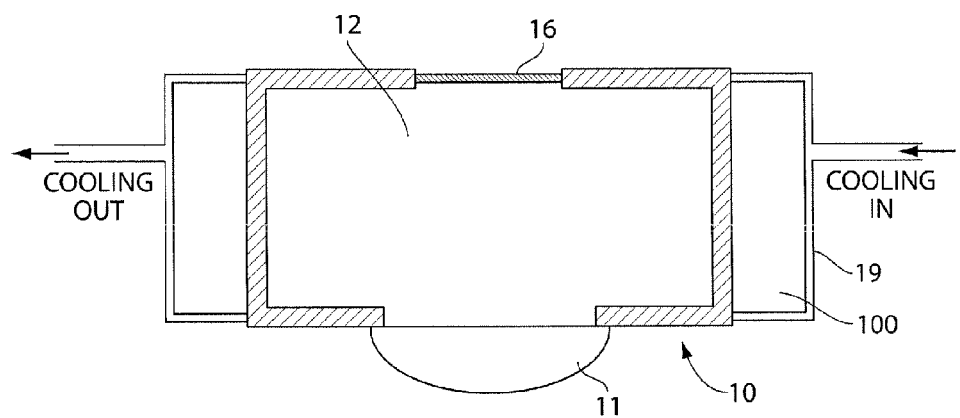
FIG. 16 is a cross sectional view of an acoustic treatment chamber having a jacketed heat exchanging system.

FIGS. 15 and 16 depict another embodiment of a processing chamber 10, where focused acoustic energy generated by an acoustic energy source 2 passes through an acoustic window 11 of the chamber and into an internal volume 12 of the chamber 10 where the sample material is located. The acoustic treatment system 1 may include a controller 20 (e.g., including a suitably programmed general purpose computer or other data processing device) that receives control information (e.g., from one or more sensors, user input devices, etc.) and correspondingly controls operation of the acoustic energy source 2 and/or other system components. While not a required feature of embodiments of the present disclosure, sample material may be provided into the internal volume 12 via an inlet 13 and is removed from the volume 12 via an outlet 14. For example, a suitable chamber may be provided as a single-use consumable item without a continuous flow-through inlet or outlet.

One or more walls of the chamber 10 may serve as, or otherwise be associated with, a thermal transfer mechanism, or heat exchanger, to dissipate any heat generated in the internal volume 12 and/or to receive heat from outside of the chamber 10 that is transferred into the internal volume 12. As can be seen in FIG. 15, the chamber 10 may include a heat exchanger 25 in the form of a plurality of radial fins. Of course, the heat exchanger 25 could be formed in other ways, such as including a Peltier device that uses electrical power to transfer heat from one location to another, an electric resistance heater, heat conducting rods, tubes or other structures, phase-changing materials used to transfer heat from one location to another, and so on. The heat exchanger 25 may be arranged to operate with any suitable thermal coupling medium, such as air or other gas, water or other liquid, or a solid material. For example, the chamber 10 may be completely or partially submerged in a liquid that serves to transmit heat with respect to the heat exchanger 25.

Close thermal coupling between water or other outside thermal coupling medium and the internal volume 12 may help control the temperature of the material in the internal volume 12 during acoustic processing. Control of the temperature of the coupling medium 4 can help control temperature in the internal volume 12. For example, the coupling medium 4 can be recirculated through a chiller, a heater, or other means to adjust the temperature of the coupling medium 4. Thus, the sample material inside the chamber 10 can be thermally linked to the coupling medium 4 temperature by careful consideration of the design of the chamber 10. The thermal coupling between the inside wall of the chamber 10 and the sample material may be tightly linked, due to high mixing, turbulence, and activity/or at the surface of the internal wall, thus creating high convective heat transfer. Heat can pass either through one or more ends of the chamber 10 (e.g., at the windows 11 and 16), or through the side walls of the vessel before being linked to the coupling medium 4 bulk temperature. Note that heat can flow in either direction, depending on the relative difference between the coupling medium and the sample material temperature, and the desired target of maintaining the sample at a target temperature to achieve the desired effect. The transfer between the chamber 10 internal wall and the coupling medium can be achieved by simple conduction through the wall to the outside surface, or the external surface area can be enhanced through the use of fins or other high heat transfer effects such as a jacketed vessel with pumped fluid.

For instance, FIG. 16 shows an illustrative arrangement in which a jacket 19 is positioned around at least part of the chamber 10 and a thermal transfer medium 100 is circulated in the space between the jacket 19 and the chamber 10 external wall. In addition, the inlet and/or outlet conduits can also be coupled to the coupling medium temperature and/or the thermal transfer medium by the use of enhanced thermal surfaces at the inlet, or outlet of the chamber 10. For example, although not shown in FIG. 16, an inlet 13 and/or outlet 14 may pass through the space between the jacket 19 and the chamber 10 so as to transfer heat with respect to the thermal transfer medium 100. Alternatively, the inlet and/or outlet medium conduit may include heat exchanger features that allow heat to be transferred with respect to the acoustic coupling medium 4.

In one embodiment, the chamber may include a heat exchanger at an outer surface arranged to exchange heat with the coupling medium. For example, the heat exchanger may include a plurality of radial fins, rods, recesses, cavities or other features that help to transfer heat with respect to the internal volume of the chamber. In some arrangements, heat may be transferred into the internal volume, whereas in other arrangements, heat may be transferred out of the internal volume, at least in part, by the heat exchanger. A temperature of a coupling medium, whether the acoustic coupling medium or other thermal coupling medium, may be controlled to affect desired heat transfer. An electric resistance heater or other heat generator may be provided with the chamber to provide an additional heat source, if desired. In another embodiment, the heat exchanger may include a heating or cooling jacket associated with at least a portion of the chamber to deliver heating/cooling fluid to a wall of the chamber. The jacket may allow a thermal coupling medium to contact the chamber while also keeping the thermal coupling medium separate from an acoustic coupling medium. This arrangement may useful, for example, where a particular type of material (such as water) is best used for acoustic coupling, while a different material (such as an antifreeze solution) is best used for thermal coupling.

Temperature, Cavitation, Particle Size, Solubility, and Pressure Management and Control.

Visual Monitoring of the Sample

Optical or video detection and analysis can be employed to optimize treatment of the sample. For example, in a suspension of biological tissue, the viscosity of the mixture can increase during treatment due to the diminution of the particles by the treatment and/or by the liberation of macromolecules into the solution. Video analysis of the sample during treatment allows an automated assessment of the mixing caused by the treatment protocol. The protocol may be modified during the treatment to promote greater mixing as a result of this assessment. The video data may be acquired and analyzed by the computer control system (i.e., part of the controller 20) that is controlling the treatment process. Other optical measurements such as spectral excitation, absorption, fluorescence, emission, and spectral analysis also can be used to monitor treatment of the sample, whether in the chamber 10 or in a flow path upstream or downstream of the chamber 10. A laser beam, for example, can be used for alignment and to indicate current sample position. In certain embodiments the visual or optical detection can be performed through a window in the reaction chamber. This window can be the upper or lower window of the chamber 10, a visual window integrated into the vessel side itself, or can be a window integrated into the transfer tubing or sample reservoir.

Temperature Control

Certain applications require that the temperature of the sample being processed be managed and controlled during processing. For example, many biological samples should not be heated above 4 degrees C. during treatment. Other applications require that the samples be maintained at a certain elevated temperature during treatment. The ultrasound treatment protocol influences the sample temperature in several ways: the sample absorbs acoustic energy and converts it to heat; the sample treatment chamber absorbs acoustic energy and converts it to heat which, in turn, can heat the sample; and acoustic streaming develops within the sample treatment chamber and the coupling medium, forcing convective heat transfer between the sample treatment chamber and the coupling medium.

The acoustic waves or pulses can be used to regulate the temperature of the solutions in the treatment chamber. At low power, the acoustic energy produces a slow stirring without marked heating. Although energy is absorbed to induce the stirring, heat may be lost rapidly through the sides of the treatment chamber, resulting in a negligible equilibrium temperature increase in the sample. At higher energies, more energy is absorbed, and the temperature rises. The degree of rise per unit energy input can be influenced and/or controlled by several characteristics, including the degree of heat absorption by the sample or the treatment chamber and the rate of heat transfer from the treatment chamber to its surroundings (e.g., the coupling medium). Additionally, the treatment protocol may alternate a high-powered treatment interval, in which the desired effects are obtained, with a low power mixing interval, in which acoustic streaming and convection are achieved without significant heat generation. This convection may be used to promote efficient heat exchange or cooling.

The sample temperature may be required to remain within a given temperature range during a treatment procedure. Temperature can be monitored remotely by, for example, an infrared sensor. Temperature probes such as thermocouples may not be particularly well suited for all applications because the sound beam may interact with the thermocouple and generate an artificially high temperature in the vicinity of the probe. Temperature can be monitored by the same controller 20 that controls acoustic waveform. The control may respond to an error signal which is the difference between the measured actual temperature of the sample and the target temperature of the sample. The control algorithm can be as a hysteritic bang-bang controller, such as those in kitchen stoves, where, as an output of the control system, the acoustic energy is turned off when the actual temperature exceeds a first target temperature and turned on when the actual temperature falls below a second target temperature that is lower than the first target temperature. More complicated controllers can be implemented. For example, rather than simply turning the acoustic signal on and off, the acoustic signal could continuously be modulated proportionally to the error signal, for example, by varying the amplitude or the duty cycle, to provide finer temperature regulation.

In the application of a bang-bang control algorithm for a multiple sample format, once a maximum temperature value has been exceeded and the sonic energy is turned off for a particular sample, an alternative to waiting for the sample to cool below a selected temperature before turning the sonic energy on again, is to move on to the next sample, or increase the flow rate of new sample material into the treatment chamber. Another alternative is to switch to a predefined "cooling" waveform which promotes convection without adding significant heat to a particular sample, and synchronizing this cycle with the introduction of new sample material to the chamber.

Cavitation Control

In some applications, it can be preferable to treat the sample with as much energy as possible without causing cavitation. This result can be achieved by suppressing cavitation. Cavitation can be suppressed by pressurizing the treatment chamber above ambient, often known as "overpressure," to the point at which no negative pressure develops during the rarefaction phase of the acoustic wave. This suppression of cavitation is beneficial in applications such as cell transformation where the desired effect is to open cellular membranes while maintaining viable cells. In other applications it may be desirable to enhance cavitation. In these applications, a "negative" overpressure or vacuum can be applied to the region of the focal zone.

The control of cavitation in the sample also can be important during acoustic treatment processes. In some scenarios, the presence of small amounts of cavitation may be desirable to enhance biochemical processes; however, when large numbers of cavitation bubbles exist they can scatter sound before it reaches the target, effectively shielding the sample.

Cavitation can be detected by a variety of methods, including acoustic and optical methods. An example of acoustic detection is a passive cavitation detector (PCD) which includes an external transducer that detects acoustic emissions from cavitation bubbles. (That is, the PCD may be external to the chamber 10, e.g., the PCD may be located in the coupling medium 4.) The signal from the PCD can be filtered, for example using a peak detector followed by a low pass filter, and then input to a controlling computer (part of controller 20) as a measure of cavitation activity. The acoustic signal could be adjusted in ways similar to those described in the temperature control example to maintain cavitation activity at a desired level.

Overpressure: Increased pressure in the chamber 10 is one technique for controlling cavitation. Overpressure tends to remove cavitation nuclei and increases the energy level required to create cavitation. Motes in the fluid are strongly affected by overpressure and so cavitation in free-fluid is often dramatically reduced, even by the addition of one atmosphere of overpressure. Nucleation sites on the chamber 10 walls tend to be more resistant to overpressure; however the cavitation tends to be restricted to these sites and any gas bubbles that float free into the free-fluid are quickly dissolved. By increasing the ambient pressure of the system, the pressures required for bubble nucleation and collapse increase, thus increasing the force imparted by collapse of the cavitation bubble. This relationship is roughly linear—that is, doubling the ambient pressure of the system doubles the resulting force of bubble collapse. Careful system design to accommodate higher overall pressures can allow this to scale by many factors. Overpressure may be applied to the treatment chamber, an array of treatment chambers, the treatment coupling medium and vessel, or to the entire system to achieve a higher than atmospheric pressure in the region of the focal zone.

Degassing: Reducing the gas content of the material fluid tends to reduce cavitation, again by reducing cavitation nuclei and making it harder to initiate cavitation. Another method of controlling cavitation or the effects of cavitation is to control the gasses that are dissolved in the sample fluid. For instance, cavitation causes less mechanical damage in fluid saturated with helium gas than in fluid saturated with argon gas.

Monitoring of Cavitation

A variety of methods may be employed to detect cavitation. For example, acoustic emissions, optical scattering, high-speed photography, mechanical damage, and sonochemicals can be used. As described above for monitoring temperature, information from cavitation detection can be used by the system to produce an output that selectively controls exposure of a sample to sonic energy in response to the information. Each of these methods to monitor cavitation are described more fully below.

Acoustic emissions: Bubbles are effective scatterers of ultrasound. The pulsation mode of a bubble is referred to as monopole source, which is an effective acoustic source. For small, generally linear oscillations, the bubble simply scatters the incident acoustic pulse. However, as the response becomes more nonlinear, it also starts to emit signals at higher harmonics. When driven harder, the bubbles start to generate subharmonics as well. Eventually as the response becomes a periodic or chaotic, the scattered field tends towards white noise. In the scenario where inertial collapses occur, short acoustic pressure pulses are emitted. An acoustic transducer can be configured to detect these emissions. There is a detectable correlation between the onset of the emissions and cell disruption.

Optical scattering: Bubbles also scatter light. When bubbles are present, light is scattered. Light can normally be introduced into the system using fiber optic light sources so that cavitation can be detected in real-time, and therefore can be controlled by electronic and computer systems.

High-speed photography: Bubbles can be photographed. This method typically requires high-speed cameras and high intensity lighting, because the bubbles respond on the time frame of the acoustics. It also requires good optical access to the sample under study. This method can give detailed and accurate data and may be a consideration when designing systems according to the invention. Stroboscopic systems, which take images far less frequently, can often give similar qualitative performance more cheaply and easily than high-speed photography.

Mechanical damage: Cavitation is known to create damage to mechanical systems. Pitting of metal foils is a particularly common effect, and detection method. There is a correlation between the cavitation needed to pit foils and to disrupt cells.

Sonochemicals: A number of chemicals are known to be produced in response to cavitation. The yield of these chemicals can be used as a measure of cavitational activity. A common technique is to monitor light generation from chemicals, such as luminol, that generate light when exposed to cavitation. Sonochemical yield usually can not be done during cell experiments but can be done independently under identical conditions, and thereby, provide a calibrated standard.

Materials for Treatment

A. Biological Materials

Many biological materials can be treated according the present invention. For example, such materials for treatment include, without limitation, growing plant tissue such as root tips, meristem, and callus, bone, yeast and other microorganisms with tough cell walls, bacterial cells and/or cultures on agar plates or in growth media, stem or blood cells, hybridomas and other cells from immortalized cell lines, and embryos. Additionally, other biological materials, such as serum and protein preparations, can be treated with the processes of the invention, including sterilization.

B. Binding Materials

Many binding reactions can be enhanced with treatments according to the invention. Binding reactions involve binding together two or more molecules, for example, two nucleic acid molecules, by hybridization or other non-covalent binding. Binding reactions are found, for example, in an assay to detect binding, such as a specific staining reaction, in a reaction such as the polymerase chain reaction where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

C. Chemical and Mineral Materials

Organic and inorganic materials can be treated with controlled acoustic pulses according to the methods of the invention. The sonic pulses may be used to commute a solid material, particularly under a feedback control regime, or in arrays of multiple samples. As with biological samples, individual organic and inorganic samples in an array can be treated in substantial isolation from the laboratory environment. Beside altering their physical integrity, materials can be dissolved in solvent fluids, such as liquids and gasses, or extracted with solvents. For example, dissolution of polymers in solvents can be very slow without stirring, but stirring multiple samples with current methods is difficult and raises the possibility of cross-contamination between samples. However, stirring of multiple samples without cross-contamination between samples can be accomplished with apparatus and methods of the present invention.

Treatment Applications

A. Altering Cell Accessibility

Sonicators can disrupt cells using frequencies around 20 kHz. It is generally thought there are two ways in which ultrasound can affect cells, namely by heating and by cavitation, which is the interaction of the sound wave with small gas bubbles in the sample. Heating occurs primarily due to absorption of the sound energy by the medium or by the container. For dilute aqueous systems, it is absorption by the container that is a main source of the heating. Heating is not desirable in some treatment applications, as described herein. The heating associated with the compression and cooling associated with the rarefaction of a sound wave is relatively small, even for intense sound.

According to aspects of the invention, controlled sonic pulses in a medium are used to treat a sample containing biological material. The pulses can be specifically adapted to preferentially interact with supporting matrices in a biological material, such as plant cell walls or extracellular matrices such as bone or collagen, thereby lessening or removing a barrier function of such matrices and facilitating the insertion of extracellular components into a cell. In this application, the cell is minimally altered and cell viability is preserved. These pulses can be caused by shock waves or by sound waves. The waves can be created external to the sample, or directly in the sample, via applied mechanical devices. In experiments where thermal effects are negligible, there typically is no lysis, unless cavitation is present. Other modes of sonic energy can have different effects than disrupting a matrix and can be used either with pre-treatment, with disrupting sonic energy, or by themselves. For, example the conditions to disrupt a matrix can be different from those to permeabilize a cell membrane.

There are many possible mechanisms by which cavitation may affect cells and there is no consensus as to which mechanisms, if any, dominate. The principle mechanisms are thought to include shear, microjets, shock waves, sonochemistry, and other mechanisms.

B. Extracting

In a variation of the method to alter cellular accessibility described above, controlled pulses in a medium can be used to treat a sample containing biological material to extract a fraction or fractions of the biological material. The pulses are specifically adapted to preferentially interact with supporting matrices, such as plant cell walls or extracellular matrices such as bone or collagen, or materials having differences in rigidity or permeability in a biological material, thereby lessening or removing a barrier function of such matrices or materials. These pulses can be caused by shock waves or by sound waves. The waves can be created external to the sample, or directly in the sample, via applied mechanical means.

The supporting matrix of a biological sample can be disrupted without disrupting one or more selected internal structures of the cells contained within the matrix. Representative examples of such samples are: i) bone, in which a rigid matrix contains living cells of interest; ii) mammalian tissue samples, which contain living cells embedded in a matrix of elastic connective tissue and "glycocalyx" or intercellular matrix; and iii) plant tissues, such as leaves, which contain cells in a matrix of cellulose, often crosslinked with other materials, of moderate rigidity. Virtually all living cells are gelatinous in texture, and can be deformed to some extent without rupture or internal damage. Matrices, in contrast, are designed to support and protect cells, as well as to achieve other biological functions. In the three examples above, the matrices of bone and leaves are designed to provide rigidity to the structure, while the support of most collagenous matrices has a strongly elastic character. Thus, different protocols for example, amplitude, duration, number of pulses, and temperature of sample, may be used to disrupt different matrices by mechanical means without damaging the cellular material.

Three areas to optimize for extraction are treatment waveform, mixing waveform, and positioning or dithering. One method to determine the appropriate treatment and positioning parameters for a target sample for extraction purposes is described below.

First, a solid sample is placed in a volume of liquid in about a 1:1 ratio (weight/volume), in a treatment chamber. For example, 0.25 ml of methanol is added to 0.25 gm of leaf tissue in a 0.5 ml treatment chamber. A single sample is placed within the focal zone of the sonic apparatus. Without using the treatment protocol, the mixing waveform is adjusted to provide "stirring" of the sample at the lowest amplitude, fewest cycles/burst, and lowest duty cycle. After the mixing waveform protocol is defined, the disruption treatment waveform is adjusted by immobilizing the target sample in the focal zone such that there is no mixing and no sample movement, such as dithering. Using a sonic energy source such as a piezoelectric transducer, the sample is subjected to a minimum number of cycles per burst, for example, three. For extraction purposes, the amplitude is initially used with a nominal 500 mV setting. A portion of the sample is treated and inspected under a microscope for signs of membrane disruption. Such inspection can be done in conjunction with dyes that stain intracellular organelles. The number of cycles/burst is then increased until a particular desired tissue disruption level is achieved in the immobilized portion of tissue. With a fresh sample, and with a 1:1 ratio of tissue to liquid, the temperature of the sample is monitored during a million cycle total treatment with an infra-red sensor directed to the top of a thin polyethylene film covering the sample vessel. The duty cycle is adjusted to keep the temperature within predefined ranges, such as 4 degrees C. within +/−2 degrees C. As discussed above, the different phases of extraction can be performed with different treatment chambers arranged in series (as in FIG. 9) or with the same chamber (e.g., where material flows in an oscillating manner through the chamber 10). The different chambers, or treatment conditions, may be adjusted to achieve the desired result for each stage in the process.

C. Introducing a Molecule into or Removing a Molecule from a Cell

Once a sample having a matrix has been sufficiently weakened or attenuated, but not to the point where a substantial number of cells contained within the matrix are killed or lysed, an exposed target cell or cells become amenable to insertion of exogenous molecules by techniques such as transfection or transformation. With some matrices, it may be convenient to isolate the cells from the matrices and then to transfect the cells. In other cases, it will be preferable, particularly in an automated system, to perform the transfection directly on the treated tissue sample, using solutions and conditions adapted from known techniques. Alternatively, in situations where a cell to be treated is not situated within a matrix, the cell can be directly treated according to the process below without having to pre-treat the matrix. While the treatment below is described mainly for transfection, methods and apparatus according to embodiments of the present invention are equally applicable to a transformation process or other processes to introduce an exogenous material into a permeabilized cell membrane.

The waveforms used to alter the permeability of a cell are refined depending on the particular application. Typically, the shock wave at the focal zone 17 is characterized by a rapid shock front with a positive peak pressure, for example about 100 MPa, and a negative peak pressure, for example about negative 10 MPa. This waveform is of a few microsecond duration, on the order of about 5 microseconds. If the negative peak is greater than about 1 MPa, cavitation bubbles may form. Cavitation bubble formation is also dependent upon the surrounding medium. For example, glycerol is a cavitation inhibitive medium; whereas, liquid water is a cavitation promotive medium. The collapse of cavitation bubbles forms "microjets" and turbulence that impinge on the surrounding material.

Sound waves, namely acoustic waves at intensities below the shock threshold, provide an alternative means of disrupting the matrix to allow access to the plasma membranes of the cells to allow transformation. Such sound waves can be generated by any known process. As biological material is subjected to subzero temperatures, for example about negative 5 degrees C., most but not all of the water is in the solid phase. However, in certain biological tissues micro-domains of liquid water still remain for several reasons, such as natural "antifreeze" molecules or regions of higher salt concentration. Therefore, as a sample temperature is varied during the treatment with sound or shock waves, microdomains of liquid water are able to form shock waves and induce cavitation bubble formation and collapse, with the resultant shear stresses that impinge on surrounding tissues. Indeed, gradual alteration of the sample temperature can be desirable, as it provides focused domains of liquid water for impingement on the surrounding material. The waves can be applied to the samples either directly, as piezoelectric pulses, or via an intervening medium. This medium may be water, buffer, stabilizing medium for the target material to be isolated, or extraction medium for the target. An intervening medium also can be a solid, formed of a material which is intrinsically solid, or of a frozen solution.

At that point, or, optionally, previously, a solution or suspension containing the material to be incorporated into the cells is added to the sample. In one embodiment, the exogenous material is incorporated into the cells in a conventional manner, as is known in the art for cells with exposed plasma membranes. In another embodiment, acoustic energy is used to transiently permeabilize a plasma membrane to facilitate introduction of exogenous materials into the cells. The exogenous material may be present in the sample during the weakening of the matrix by acoustic energy. Even when the cells remain intact, as determined by dye exclusion or other viability measurements, the process of weakening the cell matrix by acoustic energy transiently destabilizes the plasma membranes, increasing the uptake of exogenous macromolecules and structures. If a further increase in the rate of incorporation is needed, then the intensity or time of application of acoustic energy is slightly increased until the cell membrane becomes transiently permeable. For example, a gentle pulse or wave is applied to the mixture, with a predetermined amplitude. This amplitude can be determined readily in separate experiments on samples of the same type to transiently make a plasma membrane of a cell type porous, in a similar empirical manner to the steps described above for determining an appropriate treatment to disrupt a matrix. During the transient porous state, exogenous materials diffuse into the cell and the materials are trapped there once the sonic or shock pulse is removed.

A major advantage of these methods for transfection, or other incorporation of exogenous material into living cells, is that the methods are readily amenable to scale-up, to automation, and to marked reduction in sample size and reagent volume. Thus, the methods are adaptable to large scale automation, in large part because they do not require the isolation of the cells from their matrix. Additionally, these methods are amenable to a continuous flow process such as those described herein. For example, the sonic energy treatment can be different for permeabilization than for sterilization, but the sample to be treated can be flowed through an apparatus similar to that described in FIG. 7.

The number of cells per ml of media is also important factor for cellular applications to use acoustics effectively the concentration of the cells should not be too low (as the energy generated and utilized depends on the concentration of cells) or too high (viscosity is high). Additionally, with the process of permeabilization and with the mixing profile, other techniques of gene transfer may be augmented. Examples include, calcium phosphate coprecipitation, electroporation, and receptor-dependent processes.

D. Sterilizing

The terms "sterilize," "disinfect," "preserve," decontaminate," "inactivation," "disinfect," and "kill" are used interchangeably herein, unless otherwise demanded by the context. "Sterilization," namely killing of all organisms, may not be synonymous in certain operations with "decontamination," for example, when the contaminant is non-living, such as a protein or prion. These terms, typically, mean the substantial elimination of or interference with any activity of a particular organism and/or particle.

Methods for permeabilization and extraction, described above, can be modified to sterilize a sample. The apparatus and methods for sterilizing can be optimized for efficient sterilization of particular materials in particular volumes and containers. For a particular material to be sterilized, an initial set of conditions is selected. Such conditions can include selection of a type of sonic pulse generator, intensity of sonic energy, frequency of sonic energy, where relevant, and/or like variables. The conditions also can include volume, mode of transport, and/or exposure of the materials to be sterilized. Then, the initial conditions and near variants are applied to the sample, and the percentage of cells or viruses killed is determined by standard assay conditions. Further variables are selected for change. Accordingly, a zone of maximal killing of the test organism is found. Finally, other variables, such as flow rate and/or length and/or intensity of sonic exposure, are optimized to provide both a technical solution and a commercially useful solution to the problem of sterilizing a particular material. Any of these empirically determined values can be programmed into a control system of an apparatus used for sterilization to actively control sterilization, or the apparatus can have these values previously determined such that a user need only select a predetermined sterilization mode an the apparatus.

For many liquids, adequate sterilization is provided by destroying the cell walls of bacteria, fungi, and other living cells. This result is accomplished by using frequencies and wavelengths of sound which preferentially excite the membranes of the cells while minimally heating the solution until the cells are lysed. In most cellular organisms, opening the membrane and allowing the contents to mix with an extracellular fluid will kill the organism.

Viruses can be opened to the solution by similar processing. In the case of viruses, exposure of their internal nucleic acid to the solution may not be adequate to completely inactivate them, since the naked DNA or RNA can also be infectious. Adjuncts such as iodine or nucleic-acid digesting enzymes in the solution can be provided to complete the inactivation of the viruses.

E. Mixing, Stirring, and Heating

In fluid samples, including powdered and granular media and gasses, sample mixing is conventionally performed by vortexing or stirring, or other methods such as inversion of a sample containing an air space, and shaking. Vortexing is essentially achieved by mechanical motion of the entire vessel while stirring involves mechanical contact of a driven device with a fluid. Stirring is accomplished with a variety of devices, for example with propellers, impellers, paddles, and magnetic stir bars. One problem with these methods is that it is difficult to increase their scale in order to handle dozens or hundreds of sample vessels at once. Another problem with these methods is the difficulty of mixing multiple samples while keeping the each sample substantially free from contamination. As described in more detail below, methods according to the invention can use sonic energy to mix a sample while avoiding problems with contamination. Factors, such as focusing the sonic energy, as well as otherwise controlling an acoustic waveform of the sonic energy, can be used to selectively mix a sample, for example, through acoustic streaming and/or microstreaming.

A fluid sample can be mixed controllably using the systems described herein. No direct contact between the material to be mixed and the sonic energy source is required. When the material to be mixed is in a treatment chamber, the treatment chamber itself is not necessarily touched by the source and is typically coupled to the source by a coupling medium.

F. Enhancing Reactions and Separations

In certain embodiments, temperature, mixing, or both can be controlled with ultrasonic energy to enhance a chemical reaction. For example, the association rate between a ligand present in a sample to be treated and an exogenously supplied binding partner can be accelerated. In another example, an assay is performed where temperature is maintained and mixing is increased to improve association of two or more molecules compared to ambient conditions. It is possible to combine the various aspects of the process described herein by first subjecting a mixture to heat and mixing in order to separate a ligand or analyte in the mixture from endogenous binding partners in the mixture. The temperature, mixing, or both, are changed from the initial condition to enhance ligand complex formation with an exogenously supplied binding partner relative to ligand/endogenous binding partner complex formation at ambient temperature and mixing. Generally, the second temperature and/or mixing conditions are intermediate between ambient conditions and the conditions used in the first separating step above. At the second temperature and mixing condition, the separated ligand is reacted with the exogenously supplied binding partner.

Polymerase Chain Reaction ("PCR") Thermal Cycling

One of the bottlenecks of the PCR technique is cooling time. The heating cycle is rapid; however, cooling is limited by convection. Even in biochip formats, in which DNA or another target molecule is immobilized in an array on a microdevice, there is no "active" cooling process. However, certain embodiments of the invention can be used to overcome this bottleneck.

In certain embodiments, a treatment process can be used to both heat and cool the sample rapidly with little overshoot from a baseline temperature at which the primer and target to be amplified anneal. The process can be summarized as follows. A sample is treated with relatively high power sonic energy such that the sample absorbs sonic energy and is heated. Then, the sample is mixed at low power to cool the sample by forcing convection, which may be accomplished in conjunction with a cool water bath. The heating and cooling steps can be performed in the same chamber 10, or alternately in separate chambers 10, e.g., in a system like that in FIG. 9. The material can be controlled by the timing of the transfer mechanism, such as the pump, to allow discrete processing times 'in chamber' before discharging the material and bringing in new material. This can provide time for process steps such as processing, mixing, cooling and others to fully develop before introducing new unprocessed sample to the chamber.

G. Purification, Separation, and Reaction Control

Focused sonic fields can be used to enhance separations. As noted elsewhere, sonic foci can be used to diminish or eliminate wall effects in fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate the velocity and concentration gradients of a flowing stream is applicable in a wide variety of situations.

Sonic fields also can be used to minimize concentration polarization in membrane processes, including particle classification, filtration of fine particles and colloids, ultrafiltration, reverse osmosis, and similar processes. Concentration polarization is the result of the tendency of filtered material to be present at high concentration in a layer on the filter. This layer has a low fluid concentration and, thus, diminishes the rate of filtration as the filtered solution becomes more concentrated, or as the layer thickens. This layer can be stirred remotely by focused sonic energy of low to moderate intensity. Flow rate, thus, can be enhanced without significant cost in energy or membrane life.

H. Further Uses for Remotely Actuated and Controlled Solution Mixing with Sonic Energy Control of sonic energy emission, sonic energy characteristics, and/or location of a target relative to sonic energy also can be used to pump and control the flow rate of liquids, especially in capillaries; enhance chemical reactions, such as enhancing second-order reaction rates; increase effective Reynolds number in fluid flow; and control the dispensing of semi-solid substances.

By focusing sonic energy and positioning it near a wall of a chamber or another discontinuity in a fluid path, many local differences in the distribution of materials within a sample and/or spatially-derived reaction barriers, particularly in reactive and flowing systems, can be reduced to the minimum delays required for microscopic diffusion. Put differently, enhanced mixing can be obtained in situations where imperfect mixing is common.

The controller 20 may include any suitable components to perform desired control, communication and/or other functions as described above. For example, the controller 20 may include one or more general purpose computers, a network of computers, one or more microprocessors, etc., for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the acoustic energy source 2, a pump 33, etc., as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the material in a chamber 10, a video camera or other imaging device to capture and analyze image information regarding the chamber 10 or other components, position sensors to indicate positions of the acoustic transducer 2 and/or the vessel 10, and so on), user data input devices (such as buttons, dials, knobs, a keyboard, a touch screen or other), information display devices (such as an LCD display, indicator lights, a printer, etc.), and/or other components for providing desired input/output and control functions.

EXAMPLE

The following example is intended to illustrate certain embodiments of the present invention, but is not to be construed as limiting and do not exemplify the full scope of the invention.

A first single-use consumable apparatus having a cylindrical chamber similar to that shown above in FIG. 11 was manufactured. The depth D was approximately 3 mm and the width W was approximately 11 mm, giving rise to an internal volume 58 of the chamber of approximately 300 μL. The upper wall 52 of the chamber was composed of a thin layer of glass less than 1 mm thick with air located on the opposite side of the glass. The inner surface of the upper wall defining the internal volume of the chamber was substantially flat. The side wall 54 of the chamber comprised aluminum. The internal volume 58 of the chamber was sealed by a window 56 comprising KAPTON.

A second single-use consumable apparatus having a cylindrical chamber similar to that shown above in FIG. 12 was also manufactured. The depth D was approximately 6 mm and the width W was approximately 10 mm, giving rise to an internal volume 68 of the chamber of approximately 500 μL. The body 62 of the chamber was composed of stainless steel. The inner surface of the upper wall was substantially flat. The internal volume 68 of the chamber was sealed on the bottom of the chamber by a window 66 comprising KAPTON. The KAPTON window was secured to the body with an aluminum crimp cap 64.

A felopidine micronization procedure was run using the above single-use consumable apparatuses. The felopidine composition includes 1.3% polyvidone 30 (PVPK30) and 0.025% docusate sodium (AOT), 20 mg/mL. Five trials were run according to an efficiency estimation benchmark with units of W min/mg. The average particle size and polydispersity index (PDI) were measured based on a number of input parameters including chamber volume, peak incident power (PIP), duty factor (DF), cycles per burst (C/B), average power, treatment time and estimated efficiency. Results were compared with experiments run with a conventional 12×24 test tube.

TABLE 1

Results of felopidine micronization.

| Trial | Treatment Vessel | PIP | Duty Factor (DF) | C/B | Average Power (W) | Time (min) | Estimated Efficiency (Wmin/mg) | Average Particle Size (nm) | PDI |
|---|---|---|---|---|---|---|---|---|---|
| 1 | 300 μL | 175 | 10% | 1000 | 17.5 | 54 | 175 | 384.6 | 0.377 |
| 2 | 300 μL | 140 | 50% | 1000 | 70 | 15 | 175 | 386.5 | 0.322 |

TABLE 1-continued

Results of felopidine micronization.

| Trial | Treatment Vessel | PIP | Duty Factor (DF) | C/B | Average Power (W) | Time (min) | Estimated Efficiency (Wmin/mg) | Average Particle Size (nm) | PDI |
|---|---|---|---|---|---|---|---|---|---|
| 3 | 300 μL | 175 | 50% | 1000 | 87.5 | 420 | 375 | ~300 | ~0.1 |
| 4 | 500 μL | 300 | 50% | 1000 | 150 | 60 | 900 | 303.7 | 0.317 |
| 5 | Test Tube (12 × 24) | 300 | 50% | 1000 | 150 | 60 | 225 | ~900 | ~0.4 |

The results from experiments conducted with the 300 μL and 500 μL chambers yielded average particle sizes and PDI much lower than those results observed using the 12×24 test tube. The average power used in the focused acoustic treatment for the 300 μL and 500 μL chambers was equal to or less than that used for the test tube arrangement. Accordingly, the structural geometry and make-up of the 300 μL and 500 μL chambers provided for more effective acoustic processing.

It can also be observed from Trials 1 and 4 that running a transducer to transmit acoustic energy at 17.5 W power to the chamber having a 300 μL internal volume produced a combination of average particle size and PDI comparable to running a transducer to transmit acoustic energy at 150 W power to the chamber having a 500 μA, internal volume. Accordingly, processing the felopidine particles in the chamber having a 500 μL internal volume requires approximately 8.5 times more power than processing the felopidine particles in the chamber having a 300 μL internal volume to achieve a similar result. Observing trial 3, increasing the average power input to 87.5 W and the treatment time to 420 minutes resulted in an average particle size and a PDI lower than the other trials.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A system for treating a material with acoustic energy, comprising:
   a chamber having a wall with an inner side defining an internal volume, the chamber being constructed and arranged to cause reflection of acoustic energy in the chamber to form a secondary focal zone in the chamber;
   an acoustic energy source spaced from the chamber and arranged to emit acoustic energy having a frequency of about 100 kHz to 100 MHz to create a focal zone of acoustic energy in the internal volume; and
   a coupling medium arranged to transmit acoustic energy from the acoustic energy source to the internal volume, the coupling medium being liquid or solid.

2. The system of claim 1, wherein the chamber has an opening into the internal volume, an inlet to receive an inflow of material into the internal volume and an outlet to discharge an outflow of material from the internal volume, the chamber wall being substantially transparent to acoustic energy having a frequency of about 100 kHz to 100 MHz.

3. The system of claim 2, further comprising:
   a window in the opening arranged to sealingly close the opening and to transmit focused acoustic energy into the chamber for treatment of material in the internal volume, the window being generally transparent to acoustic energy having a frequency of about 100 kHz to 100 MHz.

4. The system of claim 3, further comprising:
   a housing attached to the chamber and window so that the window is exposed at a lower end of the housing, and the chamber is located in an inner space of the housing.

5. The system of claim 4, wherein the lower end of the housing and the window are submerged in the coupling medium, where the coupling medium is a liquid.

6. The device of claim 1, wherein the chamber wall comprises an acoustically reflective material.

7. The system of claim 1, wherein the chamber wall has an outer side opposite the inner side that is substantially surrounded by a gas.

8. The system of claim 7, wherein an interface between the chamber wall and the gas has a focusing effect on acoustic energy in the internal volume to create the secondary focal zone of acoustic energy in the internal volume.

9. The system of claim 1, wherein the coupling medium is liquid.

10. The system of claim 1, wherein the chamber has an opening into the internal volume, an inlet to receive an inflow of material into the internal volume and an outlet to discharge an outflow of material from the internal volume, wherein the outlet of the chamber is located at an uppermost portion of the chamber.

11. The system of claim 10, wherein the inlet of the chamber is located below the outlet.

12. The system of claim 1, wherein the chamber has a dome shape.

13. The system of claim 1, wherein the secondary focal zone has an acoustic energy intensity greater than or less than the focal zone.

14. The system of claim 1, wherein the inner side of the wall comprises one or more structural elements for forming the secondary focal zone.

15. A method of acoustically treating a sample material, comprising:
   providing a sample to be acoustically treated into an internal volume of a chamber having a wall with an inner side;
   transmitting acoustic energy, having a frequency of about 100 kHz to 100 MHz, from an acoustic energy source that spaced from the chamber;
   transmitting the acoustic energy through a coupling medium to the internal volume, the coupling medium being liquid or solid;
   creating a focal zone of acoustic energy in the internal volume; and
   reflecting acoustic energy in the chamber to form a secondary focal zone in the chamber.

* * * * *